US012385903B2

(12) United States Patent
Soon-Shiong et al.

(10) Patent No.: US 12,385,903 B2
(45) Date of Patent: Aug. 12, 2025

(54) RP182 COMPOSITIONS AND METHODS

(71) Applicant: NantBio, Inc., Culver City, CA (US)

(72) Inventors: Patrick Soon-Shiong, Culver City, CA (US); Kayvan Niazi, Culver City, CA (US)

(73) Assignee: NantBio, Inc., Culver City, CA (US)

( * ) Notice: Subject to any disclaimer, the term of this patent is extended or adjusted under 35 U.S.C. 154(b) by 993 days.

(21) Appl. No.: 17/263,409

(22) PCT Filed: Aug. 26, 2019

(86) PCT No.: PCT/US2019/048181
§ 371 (c)(1),
(2) Date: Jan. 26, 2021

(87) PCT Pub. No.: WO2020/046835
PCT Pub. Date: Mar. 5, 2020

(65) Prior Publication Data
US 2021/0293789 A1    Sep. 23, 2021

Related U.S. Application Data

(60) Provisional application No. 62/723,411, filed on Aug. 27, 2018.

(51) Int. Cl.
*G01N 33/53*    (2006.01)
*G01N 33/50*    (2006.01)

(52) U.S. Cl.
CPC ..... *G01N 33/5055* (2013.01); *G01N 2510/00* (2013.01)

(58) Field of Classification Search
None
See application file for complete search history.

(56) References Cited

U.S. PATENT DOCUMENTS

| 2006/0135424 A1 | 6/2006 | Sanguinetti et al. |
| 2010/0028418 A1 | 2/2010 | Van Vliet et al. |
| 2017/0020956 A1 | 1/2017 | Jaynes et al. |
| 2017/0202969 A1 | 7/2017 | Schlesinger et al. |

FOREIGN PATENT DOCUMENTS

| CN | 107106638 A | 8/2017 |
| CN | 108025024 A | 5/2018 |
| EP | 2 463 300 A2 | 6/2012 |
| WO | 2016/011419 A1 | 1/2016 |
| WO | 2020/046835 A1 | 3/2020 |

OTHER PUBLICATIONS

First Office Action received for Chinese Patent Application Serial No. 201980056593.4 dated Jul. 1, 2023, 15 pages. (Including English Translation).

Feinberg et al., "Structure of a C-type Carbohydrate Recognition Domain from the Macrophage Mannose Receptor", Journal of Biological Chemistry, vol. 275, No. 28, Apr. 21, 2000, pp. 21539-21548.
Cuzzolin et al., "DockBench: An Integrated Informatic Platform Bridging the Gap between the Robust Validation of Docking Protocols and Virtual Screening Simulations", Molecules, vol. 20, No. 6, May 29, 2015, pp. 1-20.
Jaynes et al., "Structure/Function Link Between Cytokine Domains and Natural and Designed Lytic Peptides Medical Promise", Small Wonders Peptides for Disease Control, 2012, pp. 21-45 (Cited from Specification).
Brown et al., "C-type lectins in immunity and homeostasis", Nature Reviews Immunology, 2018, vol. 18, No. 6, pp. 374-389 (Cited from Specification).
Hu et al., "Structural Insights into the pH-Dependent Conformational Change and Collagen Recognition of the Human Mannose Receptor", Structure, 2018, vol. 26, No. 1, pp. 60-71 (Cited from Specification).
International Search Report and Written Opinion received for PCT Application Serial No. PCT/US2019/048181 dated Jan. 3, 2020, 10 pages.
Mullin, N. P. et al., 'Characterization of ligand binding to a carbohydrate recognition domain of the macrophage mannose receptor', Journal of Biological Chemistry, 1994, vol. 269, No. 45, pp. 28405-28413.
Scodeller, P. et al., 'Precision targeting of tumor macrophages with a CD206 binding peptide', Scientific reports, 2017, vol. 7, article No. 14655, pp. 1-12.
International Preliminary Report on Patentability Chapter I received for International PCT Application Serial No. PCT/US2019/048181 dated Mar. 11, 2021, 7 pages.
Extended European Search Report received for EP Application Serial No. 19853714.4 dated Apr. 4, 2022, 11 pages.
Asciutto et al, "Phage-Display-Derived Peptide Binds to Human CD206 and Modeling Reveals a New Binding Site on the Receptor", Journal of Physical Chemistry Part B, vol. 123, No. 9, Feb. 15, 2019 (Feb. 15, 2019), pp. 1973-1982 (abstract only).
Feinberg et al., "Structural analysis of carbohydrate binding by the macrophage mannose receptor CD206", Journal of Biological Chemistry, vol. 296, Jan. 1, 2021, p. 100368.
Zlotnikov et al., "Computer simulation of the Receptor-Ligand Interactions of Mannose Receptor CD206 in Comparison with the Lectin Concanavalin A Model", Biochemistry (Moscow), Pleiades Publishing, Moscow, vol. 87, No. 1, Jan. 1, 2022 (Jan. 1, 2022), pp. 54-69.
Second Office Action received for CN Application No. 201980056593.4 dated Mar. 28, 2024, 48 pages (including English Translation).
Communication Pursuant to Article 94(3) EPC issued for EP Application No. 19853714.4 dated Aug. 5, 2024, 20 pages.

(Continued)

*Primary Examiner* — Michael D Pak
(74) *Attorney, Agent, or Firm* — Umberg Zipser LLP; Martin Fessenmaier; Priti Phukan

(57) ABSTRACT

Compositions and methods for domain-specific targeting of CD206 are presented in which selected agents bind to the carbohydrate recognition domain 4 (CRD4) and carbohydrate recognition domain 5 (CRD5) of CD206. In certain aspects of the inventive subject matter, binding is specific, leads to a conformational change of CD206, and will induce phagocytosis in tumor associated macrophages and/or M2 macrophage cell death.

10 Claims, 21 Drawing Sheets

Specification includes a Sequence Listing.

(56) References Cited

OTHER PUBLICATIONS

Jaynes et al, "Mannose receptor (CD206) activation in tumorassociated macrophages enhances adaptive and innate antitumor immune responses", Science Translational Medicine, vol. 12, No. 530, Feb. 12, 2020.
Third Office Action issued for CN Application No. 201980056593.4 dated Jun. 28, 2024, 06 pages (including English Translation).

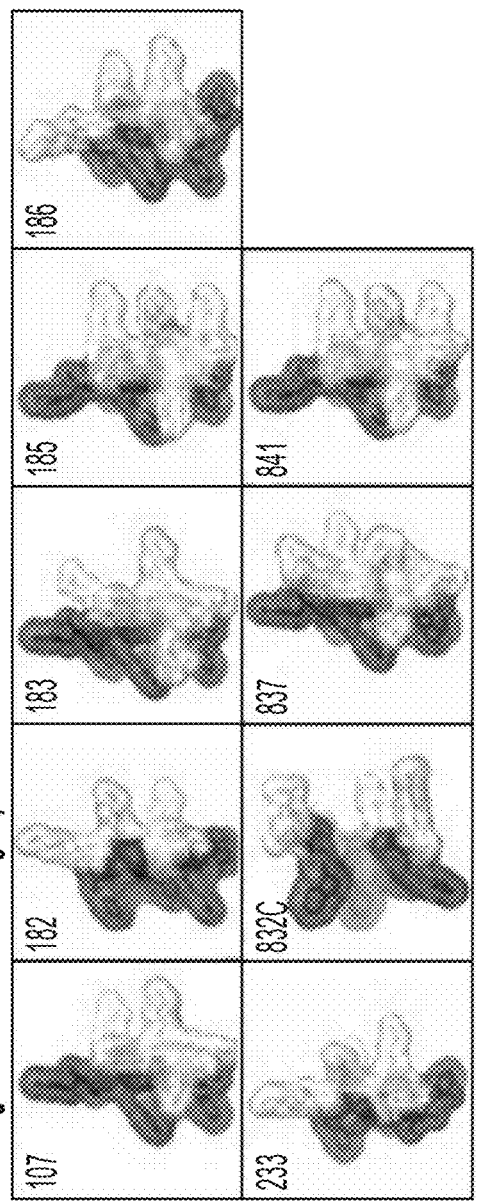
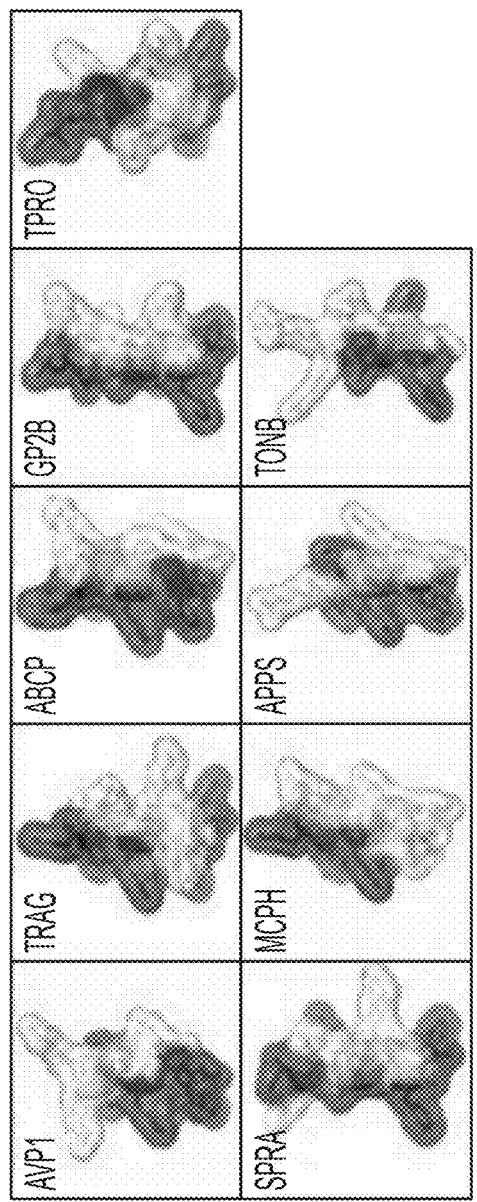
Figure 3

| | HDP | Sequence | Origin |
|---|---|---|---|
| Seq id no:6 | CATHF1 | LKKALPVAKK | ceratotoxin-A [Ceratitis capitata] Sequence ID: XP_004523341.1 |
| Seq id no:7 | CECF1 | IFKKIERVGQ | cecropin A [Hyphantria cunea] Sequence ID: AID51414.1 |
| Seq id no:8 | CECF2 | LFKKIEKVGQ | cecropin A [Hyalophora cecropia] Sequence ID: AAA29185.1 |
| Seq id no:9 | LL37F1 | FFRKSKEKIG | cathelicidin antimicrobial peptide preproprotein [Homo sapiens] Sequence ID: NP_004336.3 |
| Seq id no:10 | LL37F2 | IGKEFKRIVQ | cathelicidin antimicrobial peptide preproprotein [Homo sapiens] Sequence ID: NP_004336.3 |
| Seq id no:11 | LL37F3 | RIKDFLRNLV | cathelicidin antimicrobial peptide preproprotein [Homo sapiens] Sequence ID: NP_004336.3 |
| Seq id no:12 | LL37F4 | RIVQRIKDFL | cathelicidin antimicrobial peptide preproprotein [Homo sapiens] Sequence ID: NP_004336.3 |
| Seq id no:13 | MAGF1 | FLHSAKKFGK | magainins preproprotein [Xenopus laevis] Sequence ID: NP_001081306.1 |
| Seq id no:14 | MAGF2 | HSAKKFGKAF | magainins preproprotein [Xenopus laevis] Sequence ID: NP_001081306.1 |
| Seq id no:15 | PLEUF1 | FFKKAAHVGK | pleurocidin [Pleuronectes americanus] Sequence ID: Q90ZY0.1 |
| Seq id no:16 | PSEUF1 | ALKKVFQGIH | pseudin-2 [Pseudis paradoxa] Sequence ID: P83189.1 |
| | DHDP | Sequence | Origin |
| Seq id no:1 | 182 | KFRKAFKRFF | designed |
| Seq id no:4 | 426 | KARKAAKRAF | designed |
| | Virulence | Sequence | Origin |
| Seq id no:17 | AVP1 | EKLSAFRNFF | fibronectin-binding protein PavA [Streptococcus pneumoniae] Sequence ID:WP_079111035.1 |
| Seq id no:18 | CTPR | AVRRLAQRLA | secretion protein [Streptomyces] Sequence ID:WP_079021188.1 MULTISPECIES |
| Seq id no:19 | FLAB | MVFRDVGNRN | polar flagellin FlaB [Vibrio vulnificus YJ016B] Sequence ID: BAC95256.1 |
| Seq id no:20 | MPCP | KEFLAFKRFF | putative inner membrane protein [Chlamydia psittaci 06-1683] Sequence ID: EPJ33273.1 |
| Seq id no:21 | PTTM | GFRELFRQLD | phage tail tape measure protein [Mycobacterium obuense] Sequence ID: WP_046363070.1 |
| Seq id no:22 | TPRO | IENAAFKRFF | tail protein [Acinetobacter baumannii] Sequence ID: WP_031953720.1 |
| | Collagen | Sequence | Origin |
| Seq id no:23 | COLI | DRGIKGHRGF | pro alpha 1(I) collagen [Homo sapiens] Sequence ID: AAB94054.3 |
| Seq id no:24 | COLIV | LRGQKGDRGF | collagen type IV a6 chain [Homo sapiens] Sequence ID: AAB19038.1 |
| Seq id no:25 | COLV | EAGEKGDQGL | collagen type V alpha 3 chain [Homo sapiens] Sequence ID: AAF59902.1 |
| Seq id no:26 | COLVII | HVVQRGEHSL | collagen alpha-1(VII) chain isoform X2 [Homo sapiens] Sequence ID: XP_016861177.1 |
| Seq id no:27 | COLVIII | VLDAIRRLRL | collagen alpha-3(VI) chain isoform X3 [Homo sapiens] Sequence ID: XP_005246122.1 |
| Seq id no:28 | COLXVI | IVRRADRAAV | human type XVIII collagen [Homo sapiens] Sequence ID: CAB90482.1 |

| | Sequence | Molly | C1 BE | Ave. C2 BE | Ave. C3 BE | Ave. All C BE | C Score | Ave. NCBE | | C1 BE | Ave. C2 BE | Ave. C3 BE | Ave. All C BE | C Score | Ave. NCBE |
|---|---|---|---|---|---|---|---|---|---|---|---|---|---|---|---|
| HDP | | | | | | | | | | | | | | | |
| CATHF1 | LKKALPAKK | | -565 | -556 | -629 | -579 | 0.988 | -572 | | -423 | -464 | -433 | -420 | 0.983 | -413 |
| CECF1 | IFKKIERVGQ | | -604 | -663 | -664 | -670 | 0.980 | -657 | | -469 | -446 | -444 | -450 | 0.988 | -445 |
| CECF2 | LFKKIEKVGQ | | -599 | -596 | -599 | -610 | 0.971 | -592 | | -545 | -537 | -568 | -538 | 0.977 | -526 |
| LL37F1 | FFRKSKEKIG | | -626 | -638 | -677 | -650 | 0.981 | -635 | | -554 | -493 | -472 | -488 | 0.988 | -462 |
| LL37F2 | IGKEFKRIVQ | | -651 | -574 | -649 | -620 | 0.992 | -615 | | -451 | -466 | -455 | -466 | 0.991 | -462 |
| LL37F3 | RIKDFLRNLV | | -759 | -765 | -776 | -777 | 0.970 | -754 | | -546 | -514 | -529 | -533 | 0.983 | -524 |
| LL37F4 | RIVQRIKDFL | | -679 | -693 | -681 | -692 | 0.971 | -672 | | -554 | -601 | -576 | -541 | 0.984 | -532 |
| MAGF1 | FLHSAKKFGK | | -807 | -826 | -768 | -758 | 0.965 | -731 | | -591 | -539 | -537 | -549 | 0.989 | -543 |
| MAGF2 | HSAKKFGKAF | | -708 | -708 | -754 | -730 | 0.966 | -705 | | -519 | -530 | -514 | -515 | 0.982 | -506 |
| PLEUF1 | FFKKAAHVGK | | -709 | -711 | -701 | -717 | 0.991 | -711 | | -594 | -530 | -492 | -496 | 0.965 | -479 |
| PSEUF1 | ALKKVFQGIH | | -675 | -669 | -696 | -680 | 0.981 | -657 | | -491 | -474 | -567 | -491 | 0.970 | -476 |
| DHDP | Sequence | Molly | | | | | | | | | | | | | |
| RP182 | KFRKAFRKFF | | -889 | -908 | -881 | -903 | 0.979 | -884 | | -764 | -624 | -635 | -645 | 0.984 | -635 |
| RP426 | KARKAAKRAF | | -766 | -663 | -640 | -670 | 0.962 | -645 | | -455 | -449 | -468 | -452 | 0.979 | -443 |
| Virulence | Sequence | Molly | | | | | | | | | | | | | |
| AVP1 | EKLSAFRNFF | | -823 | -796 | -1006 | -840 | 0.969 | -614 | | -590 | -648 | -603 | -594 | 0.996 | -592 |
| CTPR | AVRRLAQRLA | | -750 | -784 | -762 | -779 | 0.975 | -760 | | -494 | -520 | -480 | -499 | 0.996 | -496 |
| FLAB | MVFRDVGNRN | | -694 | -721 | -698 | -716 | 0.986 | -706 | | -465 | -515 | -495 | -481 | 0.978 | -470 |
| MPCP | KEFLAFKRFF | | -857 | -882 | -854 | -884 | 0.972 | -859 | | -559 | -541 | -577 | -575 | 0.990 | -569 |
| PTTM | GFRELFRQLD | | -809 | -807 | -843 | -827 | 0.997 | -825 | | -573 | -650 | -559 | -584 | 0.971 | -567 |
| TPRO | IENAAFKRFF | | -870 | -838 | -837 | -847 | 0.983 | -833 | | -542 | -536 | -557 | -555 | 0.981 | -544 |
| Virulence | Sequence | Molly | | | | | | | | | | | | | |
| COLI | DRGIKGHRGF | | -796 | -819 | -789 | -817 | 0.979 | -800 | | -627 | -574 | -631 | -579 | 0.976 | -565 |
| COLIV | LRGQKGDRGF | | -719 | -761 | -701 | -720 | 0.983 | -708 | | -444 | -433 | -452 | -458 | 0.984 | -451 |
| COLV | EAGEKGDQGL | | -499 | -502 | -496 | -511 | 0.980 | -501 | | -378 | -345 | -329 | -341 | 0.981 | -335 |
| COLVI | VLDAIRRLRL | | -806 | -792 | -818 | -828 | 0.988 | -818 | | -513 | -491 | -552 | -499 | 0.989 | -494 |
| COLVII | HVVQRGEHSL | | -714 | -718 | -723 | -732 | 0.996 | -729 | | -525 | -458 | -507 | -474 | 0.969 | -459 |
| COLXVIII | NRRADRAAV | | -717 | -740 | -717 | -730 | 0.985 | -715 | | -485 | -519 | -468 | -488 | 0.991 | -484 |

Seq id no:6 CATHF1
Seq id no:7 CECF1
Seq id no:8 CECF2
Seq id no:9 LL37F1
Seq id no:10 LL37F2
Seq id no:11 LL37F3
Seq id no:12 LL37F4
Seq id no:13 MAGF1
Seq id no:14 MAGF2
Seq id no:15 PLEUF1
Seq id no:16 PSEUF1
Seq id no:1 RP182
Seq id no:4 RP426
Seq id no:17 AVP1
Seq id no:18 CTPR
Seq id no:19 FLAB
Seq id no:20 MPCP
Seq id no:21 PTTM
Seq id no:22 TPRO
Seq id no:23 COLI
Seq id no:24 COLIV
Seq id no:25 COLV
Seq id no:27 COLVI
Seq id no:26 COLVII
Seq id no:28 COLXVIII

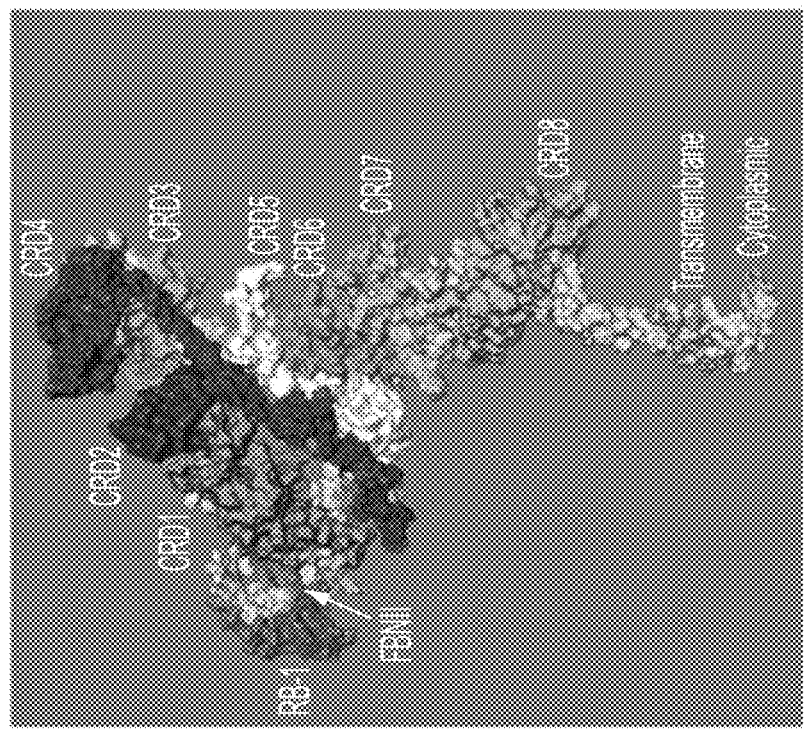
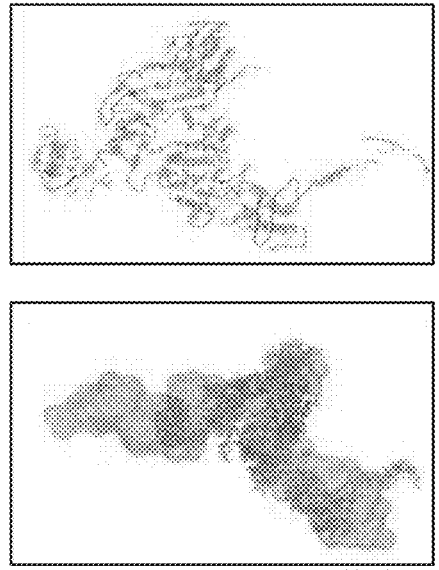
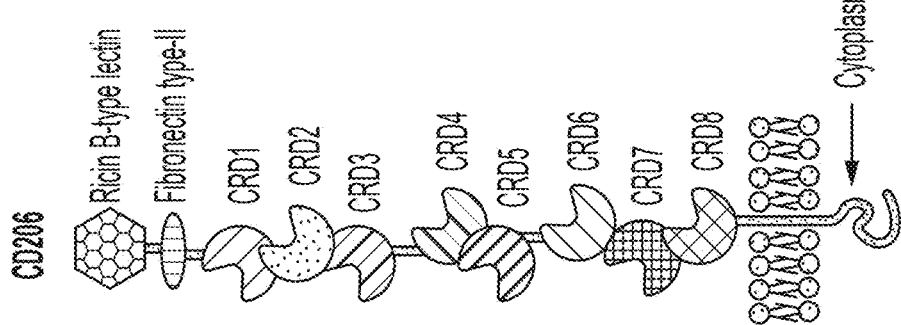
Figure 10

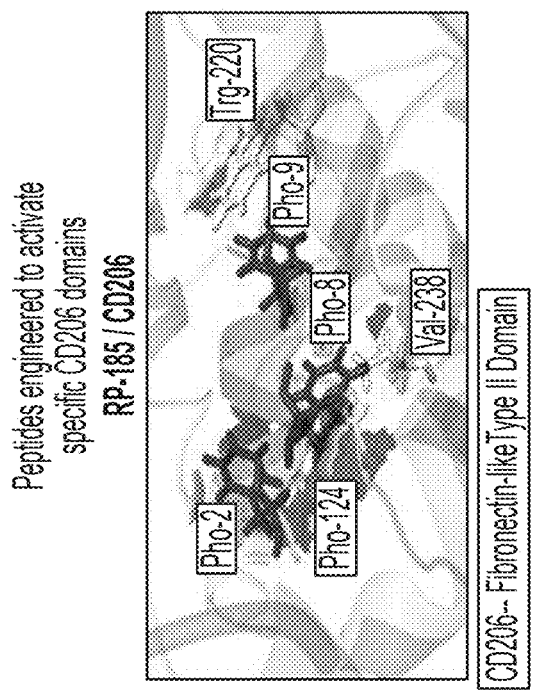
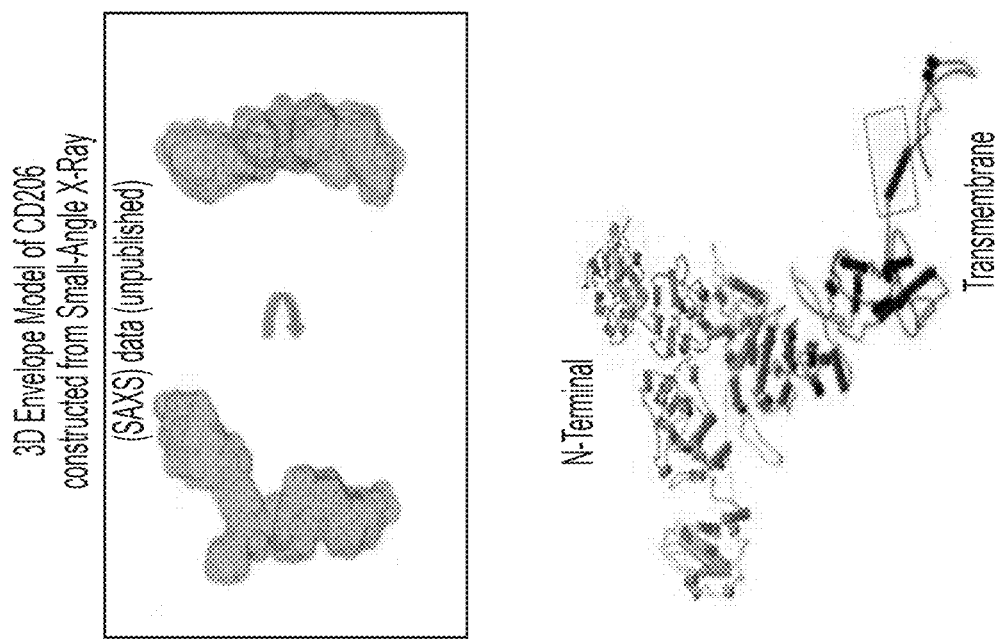
Figure 11

RP182 COMPOSITIONS AND METHODS

This application claims priority to our U.S. provisional patent application Ser. No. 62/723,411, which was filed Aug. 27, 2018, and which is incorporated by reference herein.

SEQUENCE LISTING

The content of the ASCII text file of the sequence listing named 102719.0019PCT_ST25, which is 7 kb in size was created on Aug. 23, 2019 and electronically submitted via EFS-Web along with the present application is incorporated by reference in its entirety.

FIELD OF THE INVENTION

The field of the invention is compositions and methods of targeting CD206, especially as it relates to identification and use of compounds that activate tumor associated macrophages and that reduce or eliminate M2 macrophages.

BACKGROUND OF THE INVENTION

The background description includes information that may be useful in understanding the present invention. It is not an admission that any of the information provided herein is prior art or relevant to the presently claimed invention, or that any publication specifically or implicitly referenced is prior art.

All publications and patent applications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

CD206 (mannose receptor) is a complex receptor that is often found on the surface of macrophages and is thought to recognize mannose, N-acetylglucosamine, and fucose, which are commonly found in the glycoproteins of various microorganisms. As such, CD206 seems to play a role in innate immune response. However, selective agents that modulate macrophage activity have remained elusive, in part due to the complex structure of CD206. Therefore, there remains a need for compositions and methods to selectively target CD206.

SUMMARY OF THE INVENTION

Disclosed herein are various compositions and methods of domain-specific targeting of CD206 in which selected agents bind to the carbohydrate recognition domain 4 (CRD4) and carbohydrate recognition domain 5 (CRD5) of CD206. Such binding is specific, leads to a conformational change of CD206, and will induce phagocytosis in tumor associated macrophages and/or M2 macrophage cell death.

In one aspect of the inventive subject matter, the inventors contemplate method of screening a pharmaceutical agent that includes a step of modeling or identifying an agent as a selective binder to carbohydrate recognition domain 4 (CRD4) and carbohydrate recognition domain 5 (CRD5) of CD206; a step of quantifying affinity of the agent to the carbohydrate recognition domain 4 (CRD4) and carbohydrate recognition domain 5 (CRD5) of CD206; and a step of using the agent in a pharmaceutical formulation upon confirmation of binding of the agent to the CRD4 and CRD5.

In some embodiments, contemplated methods further comprise a step of using a molecular model of CD206 in the step of modeling or identifying, further comprise a step of identifying a conformational change of CD206 upon binding of the agent, further comprising a step of in vitro binding of the agent to a macrophage, further comprise a step of in vitro testing induction of phagocytic activity by the agent, and/or further comprise a step of in vitro testing induction of apoptosis in M2 macrophages. Most typically, the agent is RP182, a RP182 derivative, or an RP182 analog (e.g., bacterial virulence protein or analog thereof, a collagen variant or analog thereof). It is also contemplated that the pharmaceutical formulation is an anticancer formulation.

Consequently, the inventors contemplate (1) use of an agent that binds to carbohydrate recognition domain 4 (CRD4) and carbohydrate recognition domain 5 (CRD5) of CD206 to induce a conformational change in CD206, (2) use of an agent that binds to carbohydrate recognition domain 4 (CRD4) and carbohydrate recognition domain 5 (CRD5) of CD206 to activate phagocytosis of tumor associated macrophages, (3) use of an agent that binds to carbohydrate recognition domain 4 (CRD4) and carbohydrate recognition domain 5 (CRD5) of CD206 to induce M2 macrophage death or shift a M1/M2 population of macrophages to a population with depleted M2 macrophage content, and (4) use of an agent that binds to carbohydrate recognition domain 4 (CRD4) and carbohydrate recognition domain 5 (CRD5) of CD206 to identify a cell expressing CD206, wherein the agent is coupled to a detectable label.

Viewed from a different perspective, the inventors contemplate a method of inducing M2 macrophage cell death, comprising a step of contacting the M2 macrophage with a compound that targets carbohydrate recognition domain 4 (CRD4) and carbohydrate recognition domain 5 (CRD5) in an amount effective to induce M2 macrophage cell death.

Alternatively, the inventors contemplate a method of shifting a M1/M2 population of macrophages to a population with depleted M2 macrophage content, comprising a step of contacting the M1/M2 population of macrophages with a compound that targets carbohydrate recognition domain 4 (CRD4) and carbohydrate recognition domain 5 (CRD5) in an amount effective to shift the M1/M2 population of macrophages to the population with depleted M2 macrophage content.

Furthermore, the inventors also contemplate a method of activating phagocytosis of tumor associated macrophages, comprising a step of contacting the tumor associated macrophages with a compound that targets carbohydrate recognition domain 4 (CRD4) and carbohydrate recognition domain 5 (CRD5) in an amount effective to activate phagocytosis of tumor associated macrophages.

For example, in such methods the compound is an RP182 analog, a bacterial virulence protein or analog thereof, or a collagen variant or analog thereof, and/or the step of contacting is performed in vivo.

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWINGS

FIG. 3 depicts structural similarity of RP peptides to microbial cell surface proteins.

FIG. 5 depicts Natural Proteins relevant to immune system activation or macrophage scavenging for comparison with RP182 and control peptide.

FIG. 6 depicts exemplary results indicating that RP182 shows higher affinity than natural ligands to C-type lectin domains.

FIG. 10 is a molecular model establishing topology of CD206 and position of key domains/amino acids.

FIG. 11 illustrates identification of specific domains targeted by RP peptides.

DETAILED DESCRIPTION

The inventors have now discovered that natural antimicrobial peptides can be used as a starting point in identifying agents that selectively interact with CD206, particularly where in silico analysis of binding candidate compounds is used in conjunction with a CD206 model. Advantageously, molecules identified as selective binders to CD206, and especially to carbohydrate recognition domain 4 (CRD4) and carbohydrate recognition domain 5 (CRD5) of CDD206, can be used as pharmaceutical agents that stimulate phagocytic activity of tumor associated macrophages and that polarize a M1/M2 macrophage population towards a population with reduced M2 content. As should be readily apparent, such agents will beneficially activate phagocytosis of tumor cells while at the same time reduce immune suppressive M2 macrophages. Notably, the inventors discovered that at least some (if not all) of the agents that bind CRD4-5 will bind selectively to these domains and induce a conformational change in the CD206, likely providing a specific signal to the macrophage.

For example, one active compound (RP182) was derived from natural antimicrobial peptides which mimic microbial cell surface proteins and showed a significant effect in activating immune cells via a shift in macrophage population towards an activated/phagocytic M1 phenotype. Further synthetic analogues were then engineered as is shown in more detail below and screened for both CD206 binding, induction of conformational changes, and biological effect on various cell populations, and particularly macrophages. In the course of their investigation, the inventors discovered that the target receptor for such compounds was CD206. In confirmatory experiments, RP182 was shown to have far higher affinity than various natural ligands. Moreover, use of a novel 3D modeling of CD206 allowed identification of the specific target domains as well as prediction of conformational change (which was experimentally validated as is shown in more detail below).

As will be readily appreciated, agents binding to CD206, and especially to the carbohydrate recognition domain 4 (CRD4) and carbohydrate recognition domain 5 (CRD5) will be particularly beneficial in the manufacture of pharmaceutical compositions that are immune stimulating/activate tumor associated macrophages, and that reduce the number of M2 macrophages that have immune suppressive function in a tumor microenvironment.

Figure 1:
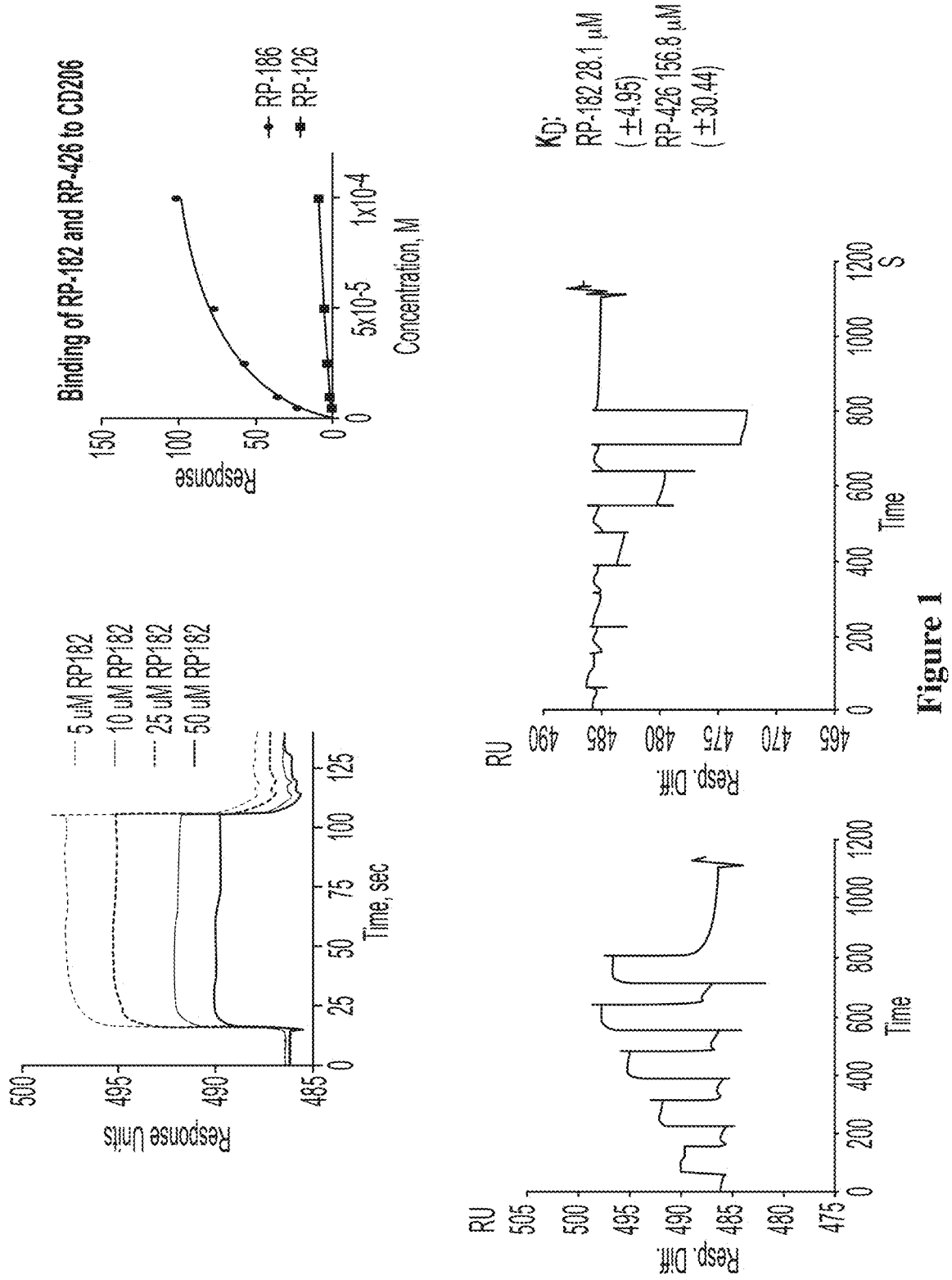
FIG. 1 shows exemplary results for RP182 binding to CD206 (vs control peptide RP426).
Figure 2:
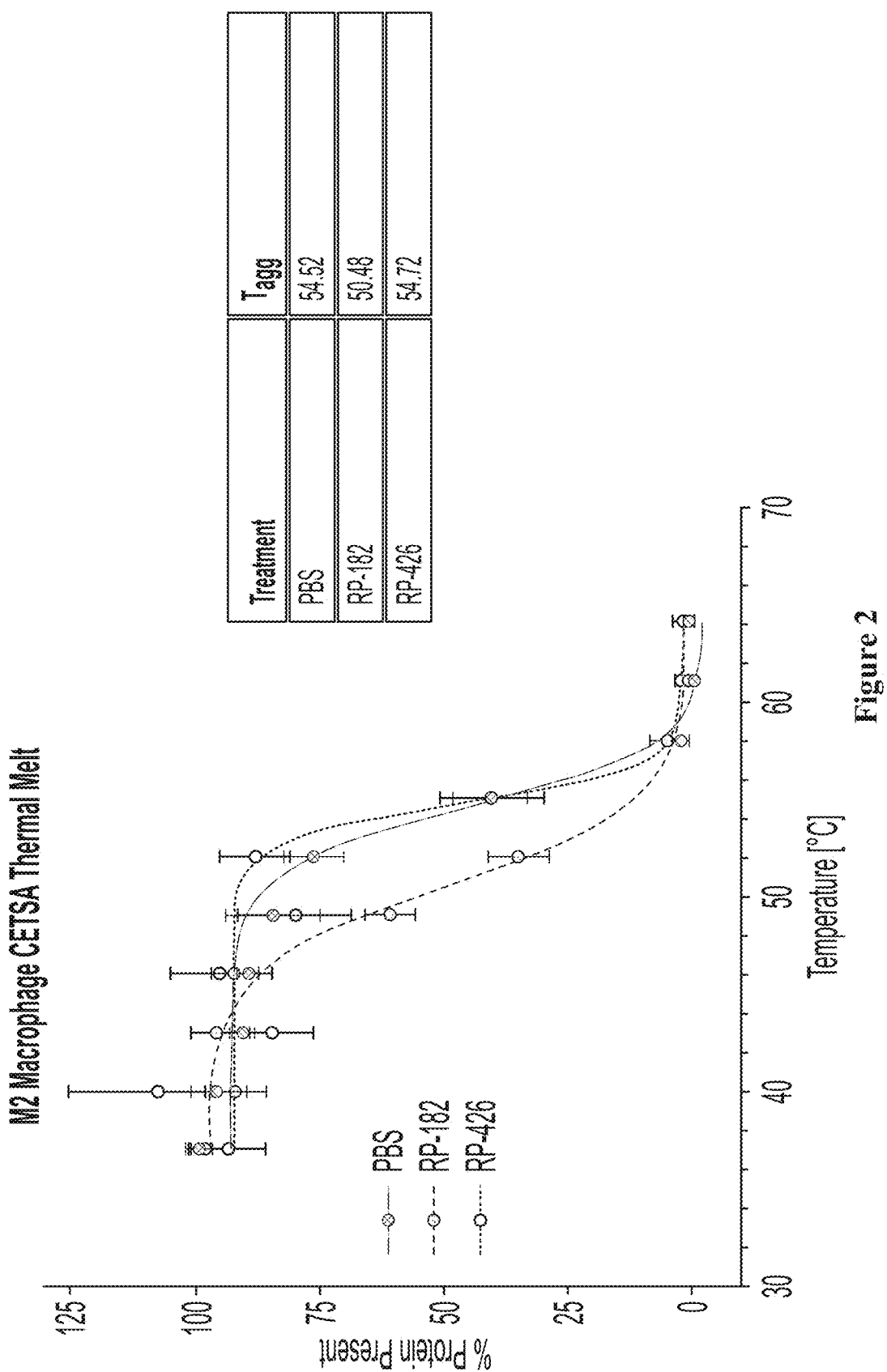
FIG. 2 shows exemplary results for specific target engagement PBS vs. RP-182 over an indicated temperature range.

Based on earlier considerations (not shown), the inventors first confirmed that RP182, a compound derived from natural antimicrobial peptides, indeed bound to CD206. To that end, an SPR analysis was performed in which binding of RP182 to CD206 was quantified. As can be seen from FIG. 1, RP182 selectively and tightly bound to CD206, whereas a control peptide (RP426) had significantly less binding affinity. FIG. 2 depicts the results of a further confirmatory experiment in which a cellular thermal shift assay (CETSA) was performed to demonstrate target engagement. Here, negative control (PBS) was compared with RP182 and control peptide RP426. As can be seen the Tagg values (average and SD from two independent experiments performed in duplicate) clearly demonstrate specific interaction with RP182 over control.

Figure 4:
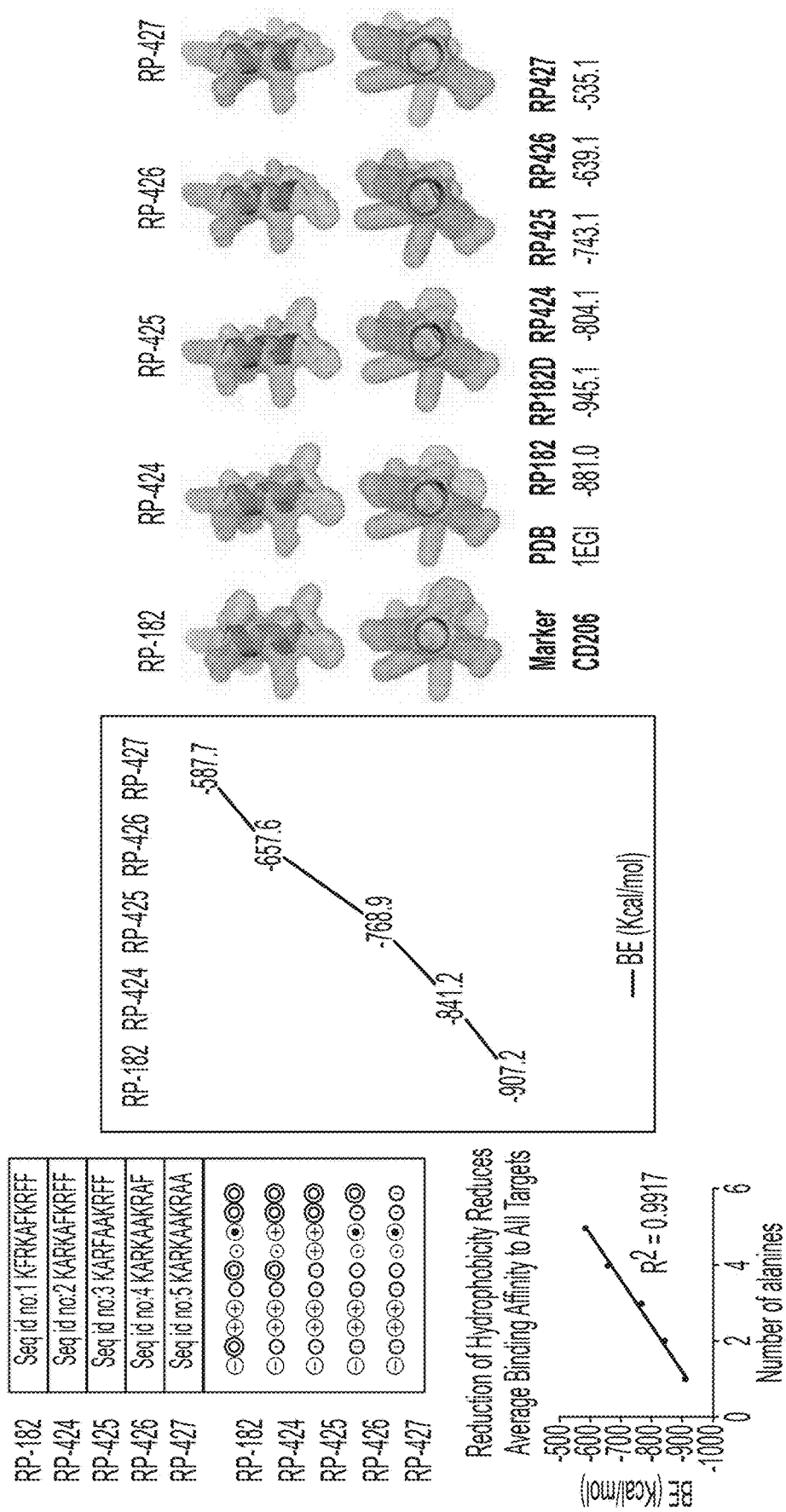
FIG. 4 depicts an exemplary illustration of a design process for CD206 ligands.
Figure 7:
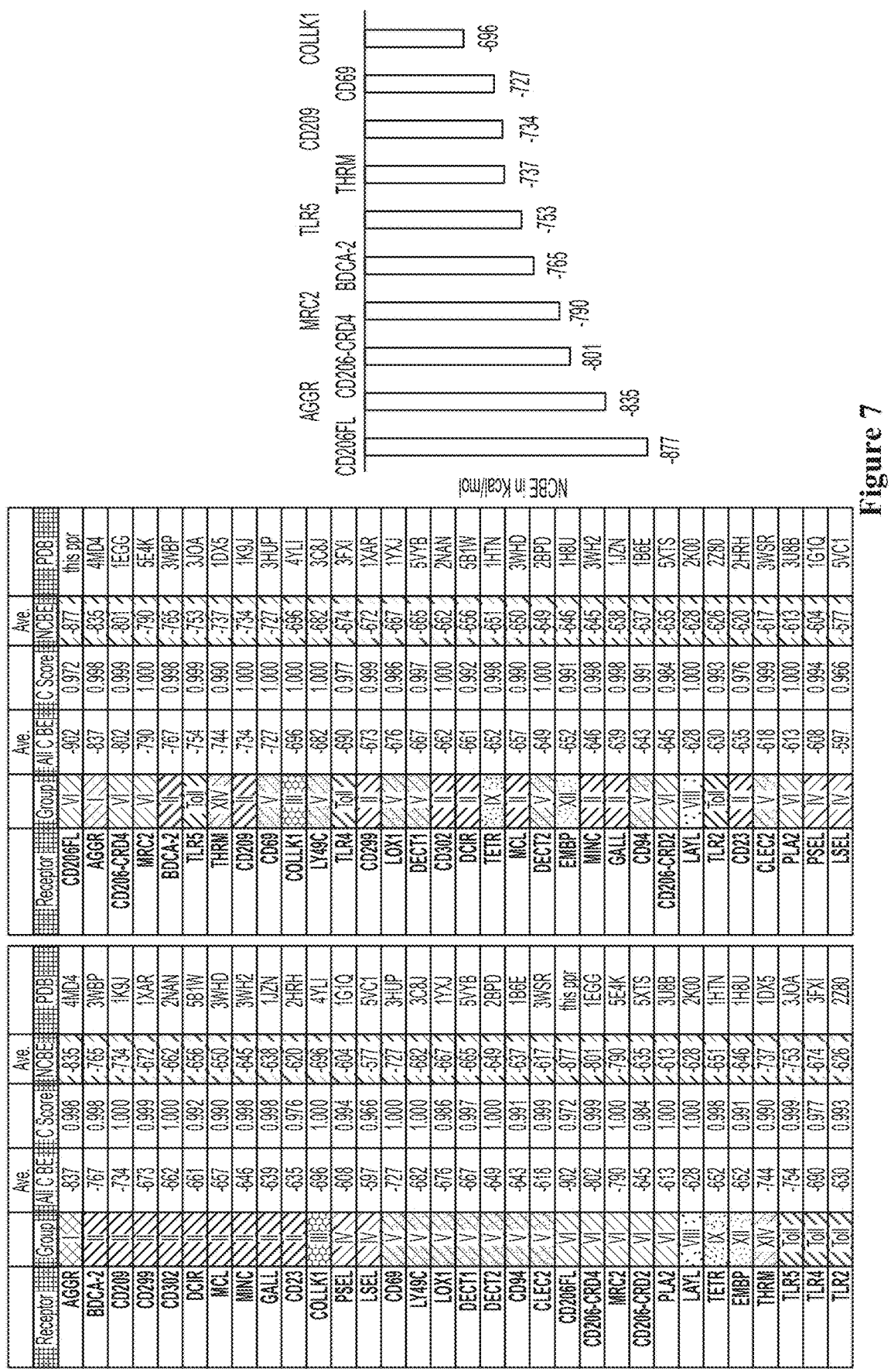
FIG. 7 depicts exemplary results leading to the Identification in silico of the mannose receptor CD206 as the specific C-type lectin receptor target of RP182.
Figure 8:
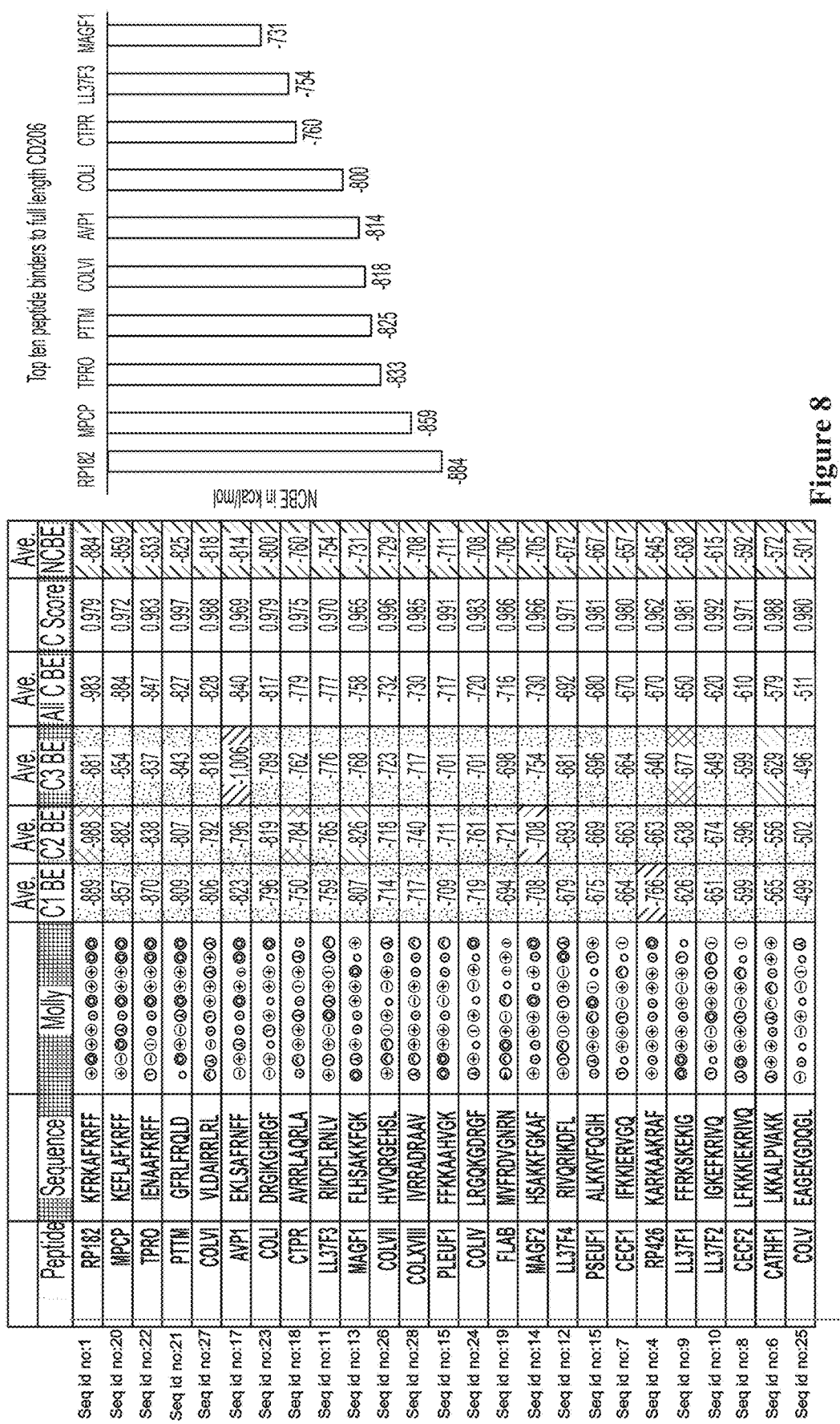
FIG. 8 depicts exemplary data in which RP182 shows higher affinity to CD206 than any natural peptide evaluated.
Figure 9:
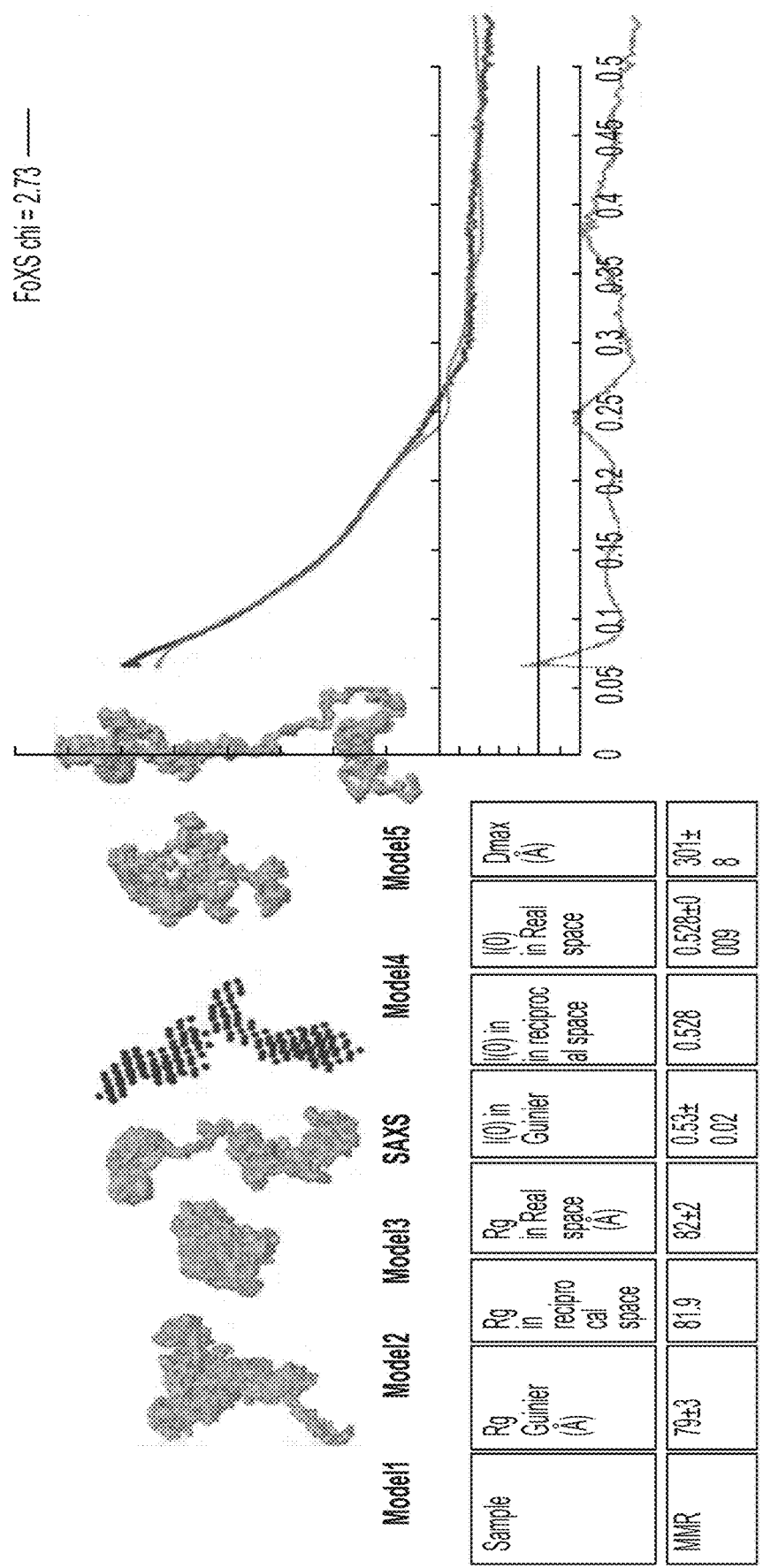
FIG. 9 depicts a number of possible structural models of CD206 and derived the best-fit model to fit small-angle x-ray data.
Figure 12:
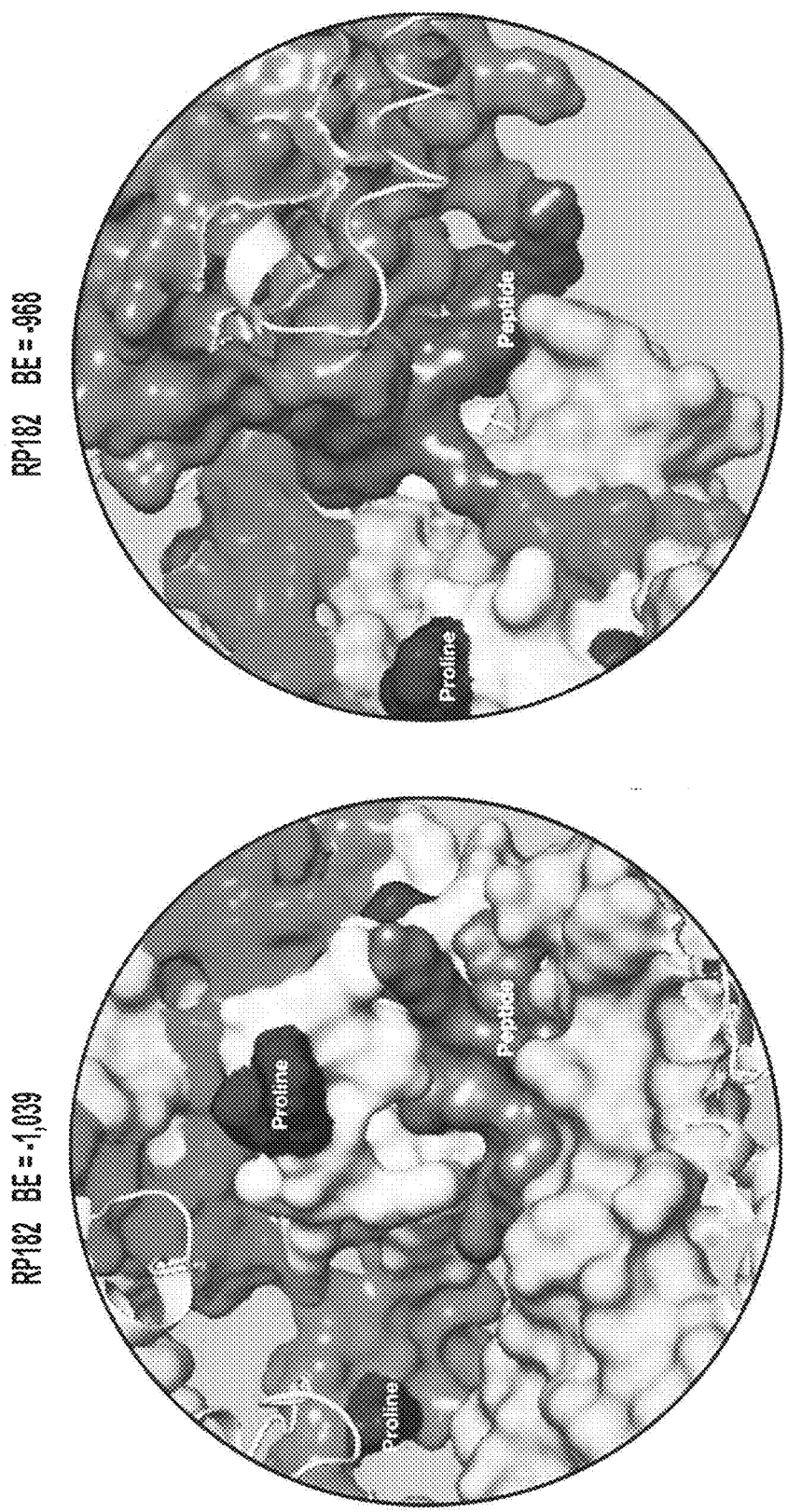
FIG. 12 shows predicted RP182 docking and conformational change in CD206 receptor.
Figure 13:
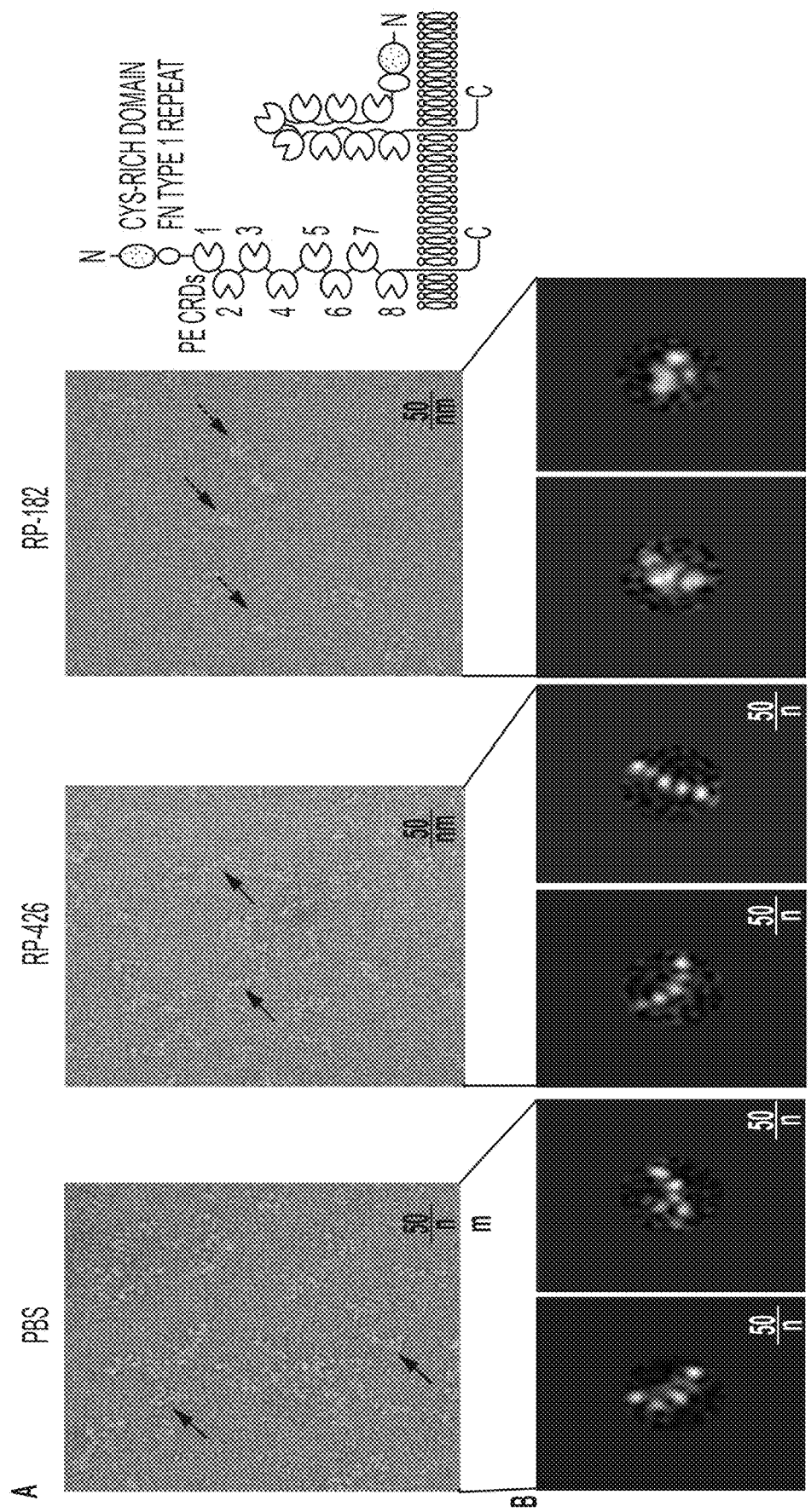
FIG. 13 depicts results from electron microscopy to verify conformational change with RP182 treatment.

To validate the concept that various synthetic peptides will mimic antimicrobial peptides, structural modeling was performed and exemplary results for the comparison are provided in FIG. 3 with synthetic peptides on the top and antimicrobial peptides on the bottom. A large number of additional variants of peptide fragments were further evaluated in silico and selected peptides were followed up with activity screening. Notably, in this process it was established that reducing hydrophobicity by substituting alanine for other amino acids with otherwise similar characteristics produced predicted increases in affinity to a variety of possible targets (initially including NFkB, TRAIL, CD206 and others). As CD206 became confirmed as the target, in silico calculations of predicted affinity were generated using ClusPro models (see also later Figures with 3D model of CD206). FIG. 4 depicts selected peptides and binding calculated energies, along with structural predictions of the peptides. The synthetic sequences shown in FIG. 4 have a peptide sequence of SEQ ID NO: 1, SEQ ID NO: 2, SEQ ID NO: 3, SEQ ID NO: 4, and SEQ ID NO: 5. FIG. 5 lists further exemplary peptides of natural origin with similarity to RP182. The sequences shown in FIG. 5 have a peptide sequence according to SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, and SEQ ID NO: 28. As such, it should be appreciated that all of these peptide sequences and analogs thereof are deemed appropriate for use herein. For example, host defense proteins that best fit the immune-modulating peptide structure/function paradigm domain, were found at URL: aps.unmc.edu/AP/main.php utilizing Molly font. A survey of this database yielded 129 of the 431 peptides listed or 29.93% that possess a domain consistent with the structural determinants necessary for activity. RP182 was optimized for maximum amphipathy, hydrophobicity and positive charge density as visualized in Molly font. RP426 is a control that tests the importance of hydrophobicity for activity. Molly font is described in: "Structure/Function Link Between Cytokine Domains and Natural and Designed Lytic Peptides: Medical Promise (2012)." Jesse M. Jaynes and Gregory C. Bernard. In Small Wonders: Peptides for Disease Control, 21-45. American Chemical Society, incorporated by reference herein. And the peptides in the Virulence and Collagen sections were selected in a similar fashion from the proteins found in the protein database at URL: www.ncbi.nlm.nih.gov.

There are 17 different human C-type Lectin groups that have been described, see "C-type lectins in immunity and homeostasis." Brown, G D, et al. Nat Rev Immunol. 2018 June; 18 (6): 374-389. A complete list of all known members can be found in the animal lectin database at the URL: www.imperial.ac.uk/research/animallectins/ctld/mammals/humanvmousedata. html. From this resource, there are 88 different C-type lectin human proteins listed. Of these 88 proteins, 28 were selected to study in silico as crystal structures were available, along with 3 different toll-like receptors. Utilizing ClusPro, the crystal structures were interrogated for binding to individual 10 mer sequence of the shown biosimilars. Biosimilars were selected based on those most similar to the 10 mer sequence within each class. The tables to the left in FIG. 6 display the results, first, as ranked according to group and second, as ranked according to the average of the normalized cluster binding energies (NCBE). The three lowest binding energies (in kcal/mol) are shown for each receptor/ligand combination. The first section compares the in silico binding of all peptides to the 28 selected human C-type lectins described in this publication. Further columns display the results, first, as ranked according to group with -BE listed, and second, as ranked according to the average of the normalized cluster binding energies (NCBE).

Using ClusPro, the crystal structures of 28 human C-type lectins and TLRs were then interrogated for binding to RP182. The two tables in FIG. 7 to the left display the results, first, as ranked according to group and second, as ranked according to the average of the normalized cluster binding energies (NCBE). The top ten of the lowest binding protein/ligand pairs are depicted in the graph to the right.

Next, to confirm selectivity of binding of RP182 to MRC1/CD206 compared to other biosimilars, the inventors repeated above docking studies of biosimilars and RP182 using the SAXS-derived full-length CD206 structure. The last section data were derived from in silico measurements using the crystal structure PDB 5XTS described in "Structural Insights into the pH-Dependent Conformational Change and Collagen Recognition of the Human Mannose Receptor." Hu Z, et al. *Structure.* 2018 Jan. 2; 26 (1): 60-71. Results are shown in FIG. 8. As can be seen, RP182 also showed higher binding affinity to full-length CD206 than any of the natural peptides chosen for their relevance to immune activation or macrophage scavenging.

In further work, various structural models of CD206 were developed and a best-fit model was derived to fit small-angle x-ray data. See FIG. 9. This model was then used for subsequent peptide design work as follows and is shown in FIG. 10. Here, human macrophage mannose receptor 1 protein (also called MMR-1 or CD206) is a single pass type I membrane signaling protein. The key topological features are the large extracellular region (1371 aa) followed by a helical transmembrane (TM) domain and a relatively small cytoplasmic region (46 aa). The protein sequence (1,456 aa) for the human CD206 was obtained from UniProt (UniProt ID P22897-1 NCBI ID: NP_002429.1) and includes two N-terminal domains (Ricin-B-type Lectin and a Fibronectin type-II) followed by eight C-type lectin domains (numbered 1 to 8) and a TM and cytoplasmic domains. 3D structural information for human CD206 is only available for a very small segment (644-787 aa; C-type lectin 4 domain). In this work, the inventors have constructed a complete 3D model for CD206 using one of the most reliable (based on CASP experiments) approaches championed by the Iterative Threading and ASSEmbly Refinement software, I-TASSER (web server version; URL: zhanglab.ccmb.med.umich.edu/I-TASSER/for model construction was used). I-TASSER utilizes a hierarchical approach that identifies 3D templates from the RCSB-PDB (www.rcsb.org) using the multiple threading approach. Finally, full-length models were constructed by iterative template fragment assembly simulations. To further assist the modeling, the inventors have provided distance restraint disulfide bond information that was identified using sequence similarity as distance restraint input. The I-TASSER identified top threading templates were 5ao5, 3jav, 5ao6 and 4igl. The normalized B-factor values for the models fluctuated around zero indicating the local accuracy of the model(s). In I-TASSER, the model confidence is measured by C-score. The C-score ranges between −5 and 2, and a higher value indicates higher confidence. The top 4 models had the following C-scores, −0.35, −1.93, −2.89 and −2.97.

The top 4 models were analyzed and the top ranked I-TASSER model based on the comparison of Small Angle X-ray Scattering model (SAXS; see A) and the I-TASSER confidence and C-scores were identified as a possible structural fold for CD206. The middle panel demonstrates the I-TASSSER first rank model in detail. The fibronectin type-II domain appears to be buried and surrounded partially by the c-terminal end region of Ricin and the C-type Lectin-1 domains. The other C-type lectin domains appear to be tightly packed. The helical transmembrane domain is followed by two short helical regions of the cytoplasmic domain. Right panel is the surface model generated in Pymol.

The so obtained model was then used to identify specific CD206 domains targeted by RP peptides as is exemplarily shown in FIG. 11. Notably, as is seen from FIG. 12, the model predicts RP182 docking and a conformational change in the CD206 receptor. To confirm that the conformational change was indeed not an artifact, the inventors used electron microscopy of CD206 in the presence and absence of RP182, and typical results are shown in FIG. 13.

Further in vitro experiments demonstrated that binding of ligands to the carbohydrate recognition domain 4 (CRD4) and carbohydrate recognition domain 5 (CRD5) had various desirable effects, including (a) strong and selective binding to CD206 (SPR, microscale thermophoresis, cellular thermal shift assay), (b) strong and selective binding to CD206+ cells, (c) induction of conformational change in CD206 molecule, (d) stimulation of phagocytic activity, and (e) reduction of M2 macrophages as is detailed below.

Figure 14:
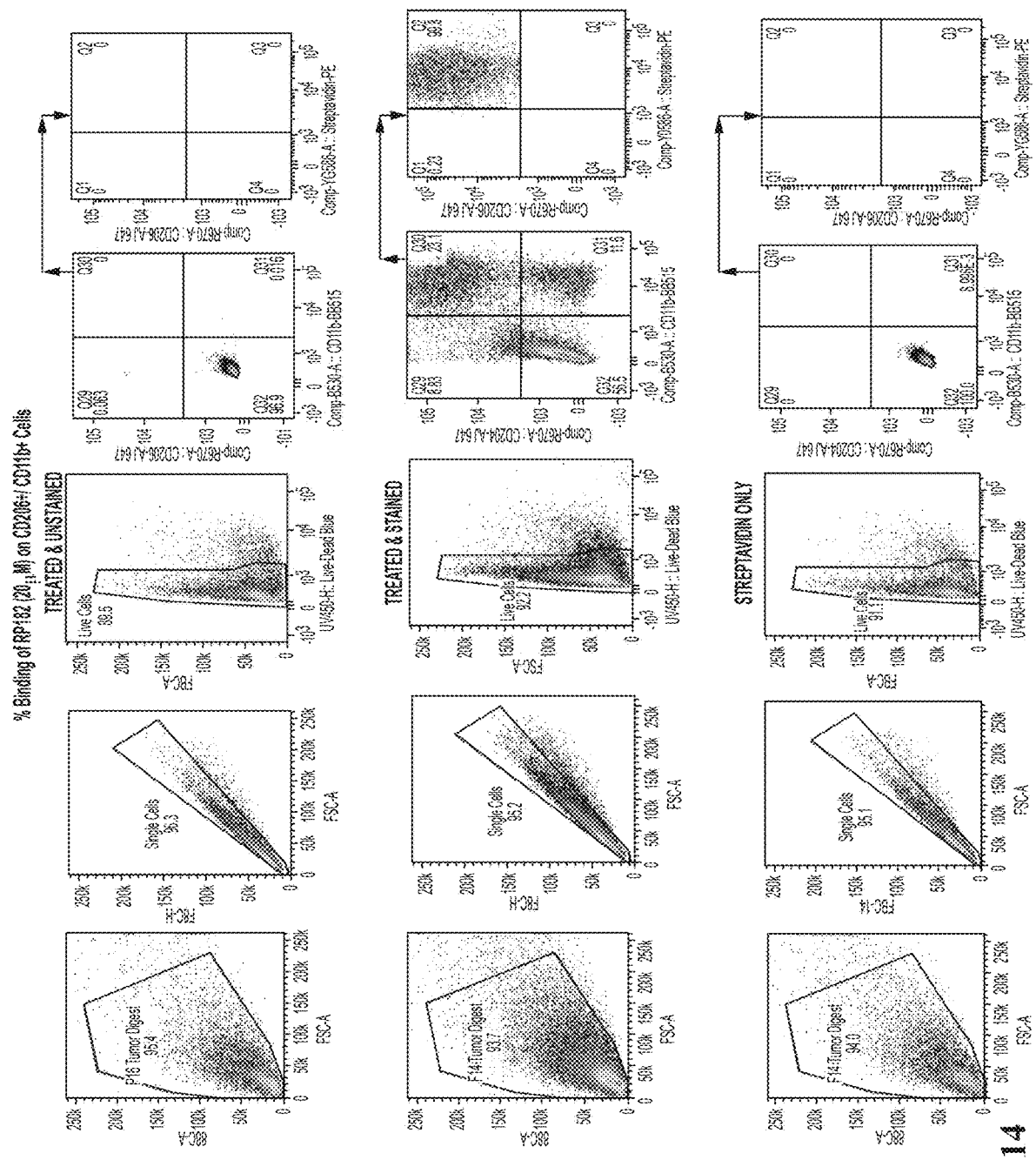
FIG. 14 depicts results for % Binding of RP182 (20 μM) on CD206+/CD11b+ Cells.
Figure 15:
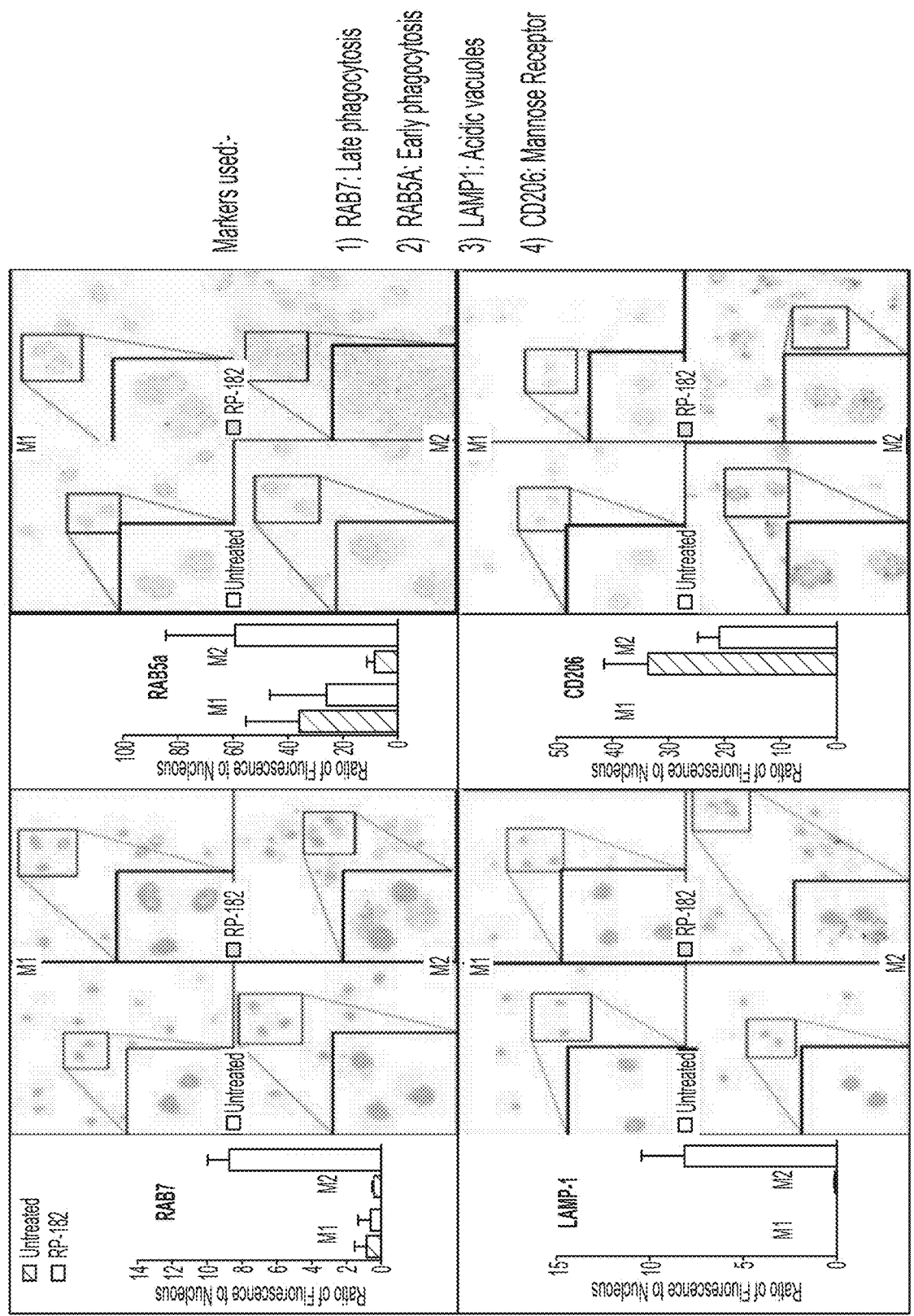
FIG. 15 depicts results showing that RP182 stimulates phagocytic activity.

More particularly, FIG. 14 depicts FACS results for binding of an exemplary compound (RP182) to CD206+ CD11b+ cells, whereas FIG. 15 depicts the results for selective stimulation of phagocytosis, autophagy, and apoptosis in M2-polarized macrophages. As can be seen from the Figure, RP-182 induced early and late phagocytosis without affecting CD206 levels after 2 hours of treatment with RP-182. Immunofluorescence of BMDMs polarized into M1 and M2 and stained with anti-Rab5, etc., RP182 but not control peptides RP-426 and MART-1 induced phagocytosis in M2-polarized macrophages. Moreover, RP182 induced apoptosis (measured by cleaved caspase; left) and autophagy (measured by anti-LC-3; right), selectively killed mouse and human M2-polarized macrophages, but did not repolarize M2 to M1 macrophages. No production as a measure of M1 function is not increased after treatment of M2 macrophages with RP-182.

Figure 16:
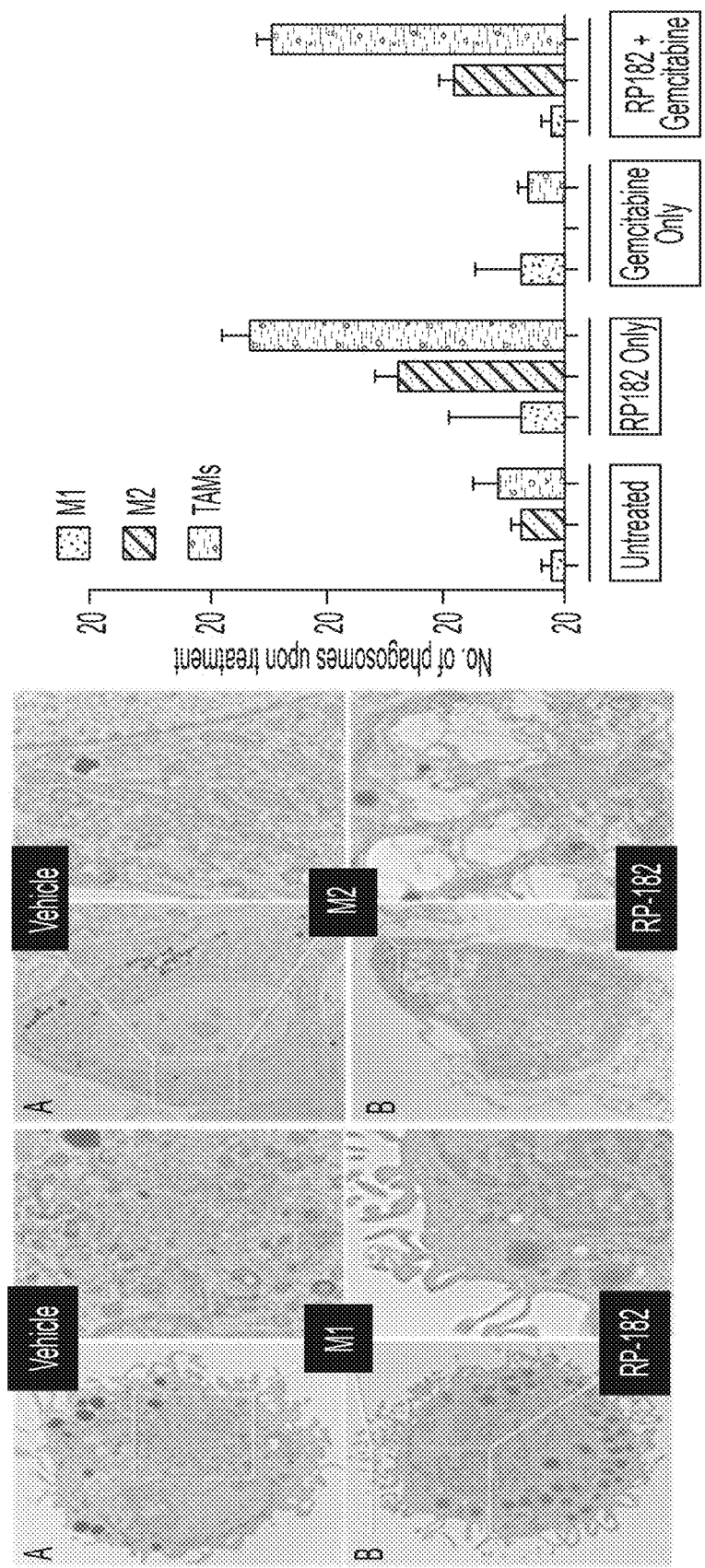
FIG. 16 depicts results showing that RP182 stimulates phagocytosis among M2-like macrophages and TAMs.
Figure 17:
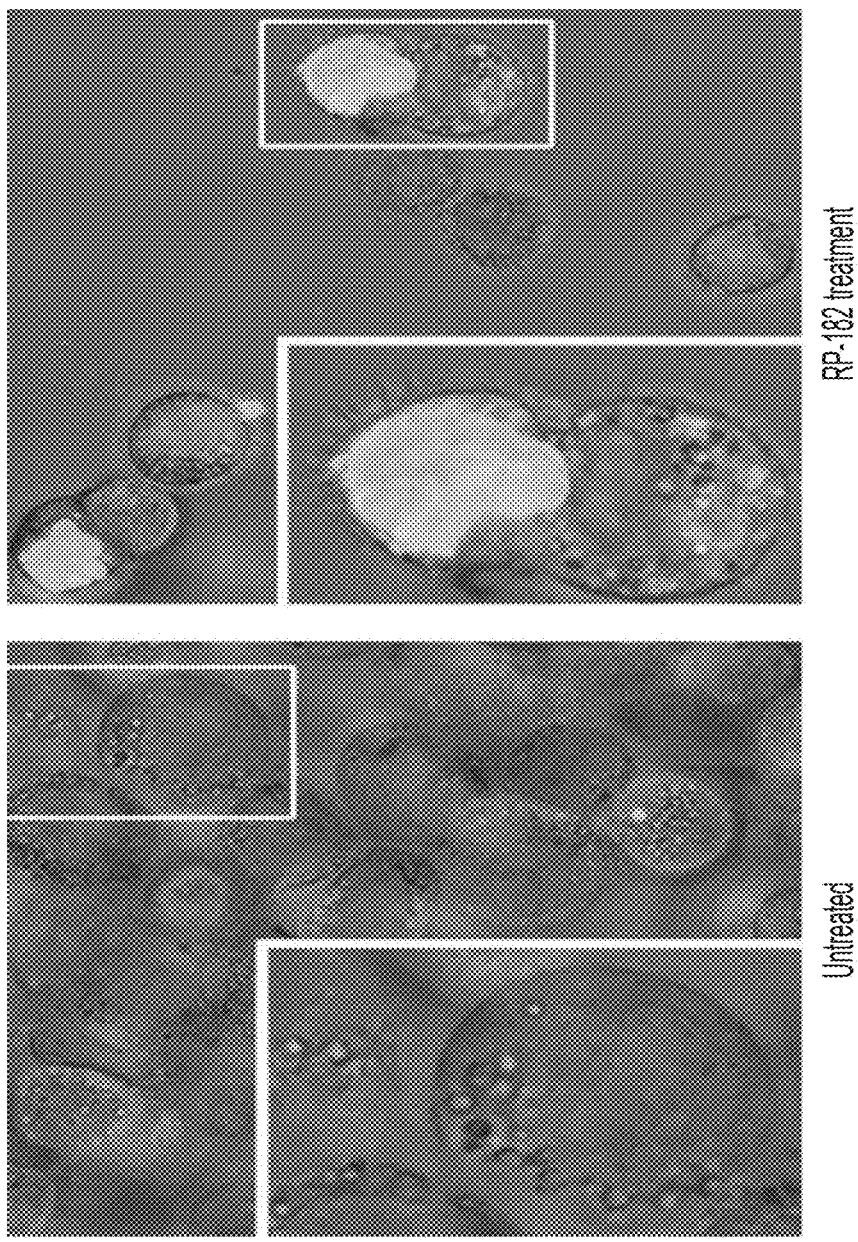
FIG. 17 depicts results showing phagocytosis of labeled KPC cells after RP182 treatment.
Figure 18:
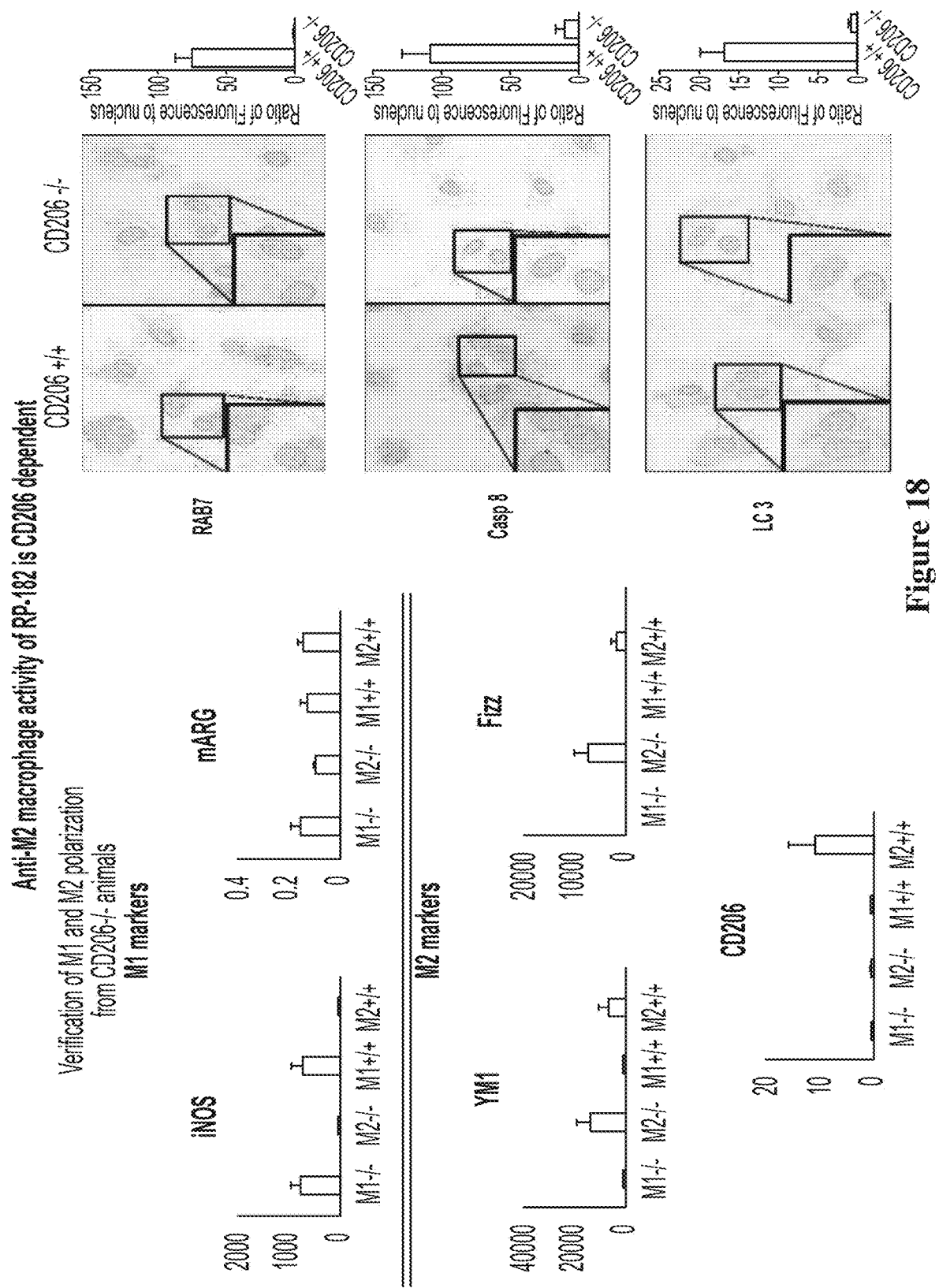
FIG. 18 depicts results showing that Anti-M2 macrophage activity of RP-182 is CD206 dependent.
Figure 19:
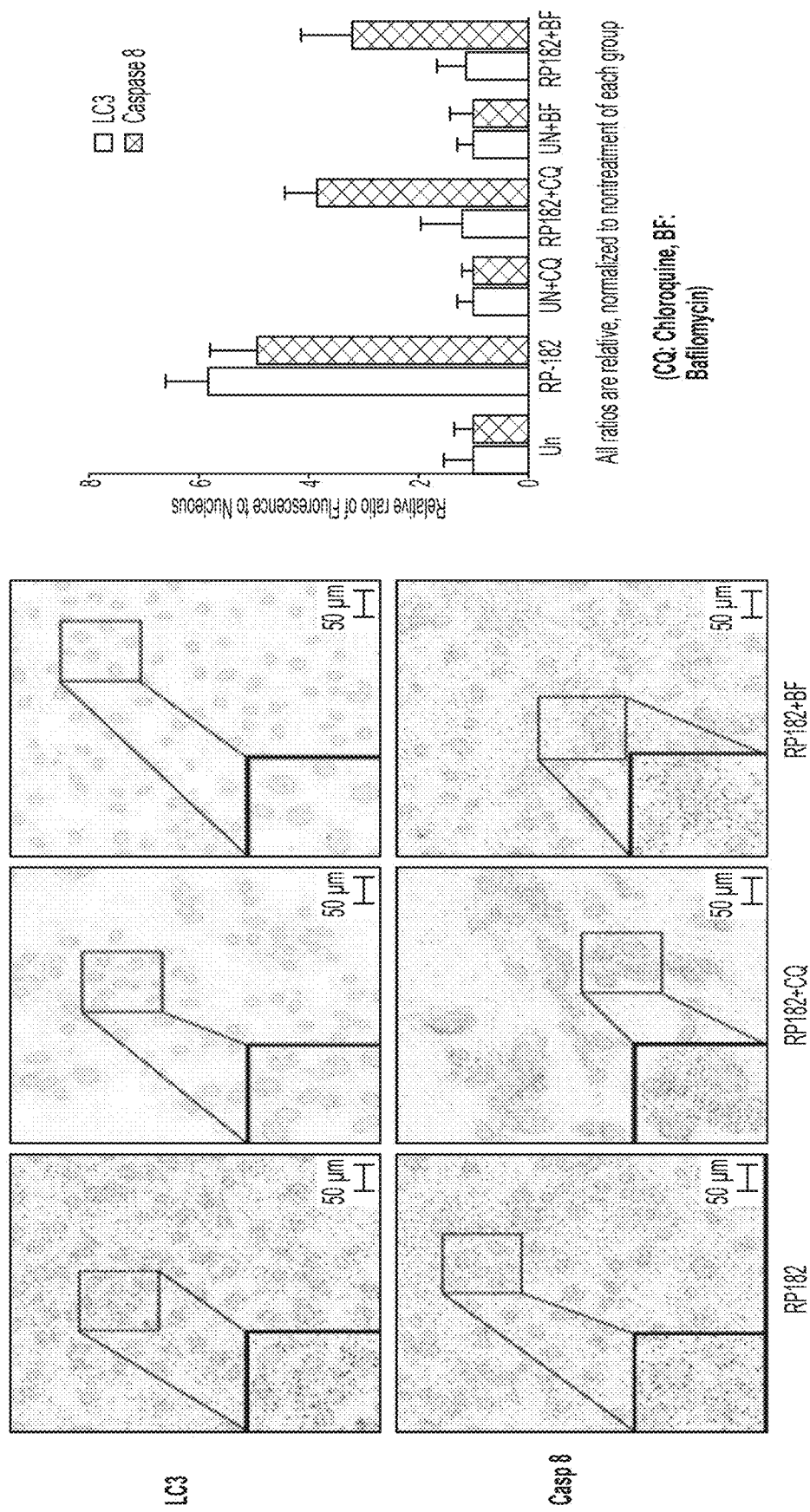
FIG. 19 illustrates determination of Autophagy and Apoptosis by RP182 peptide on M2 macrophages in presence of autophagy inhibitors.
Figure 20:
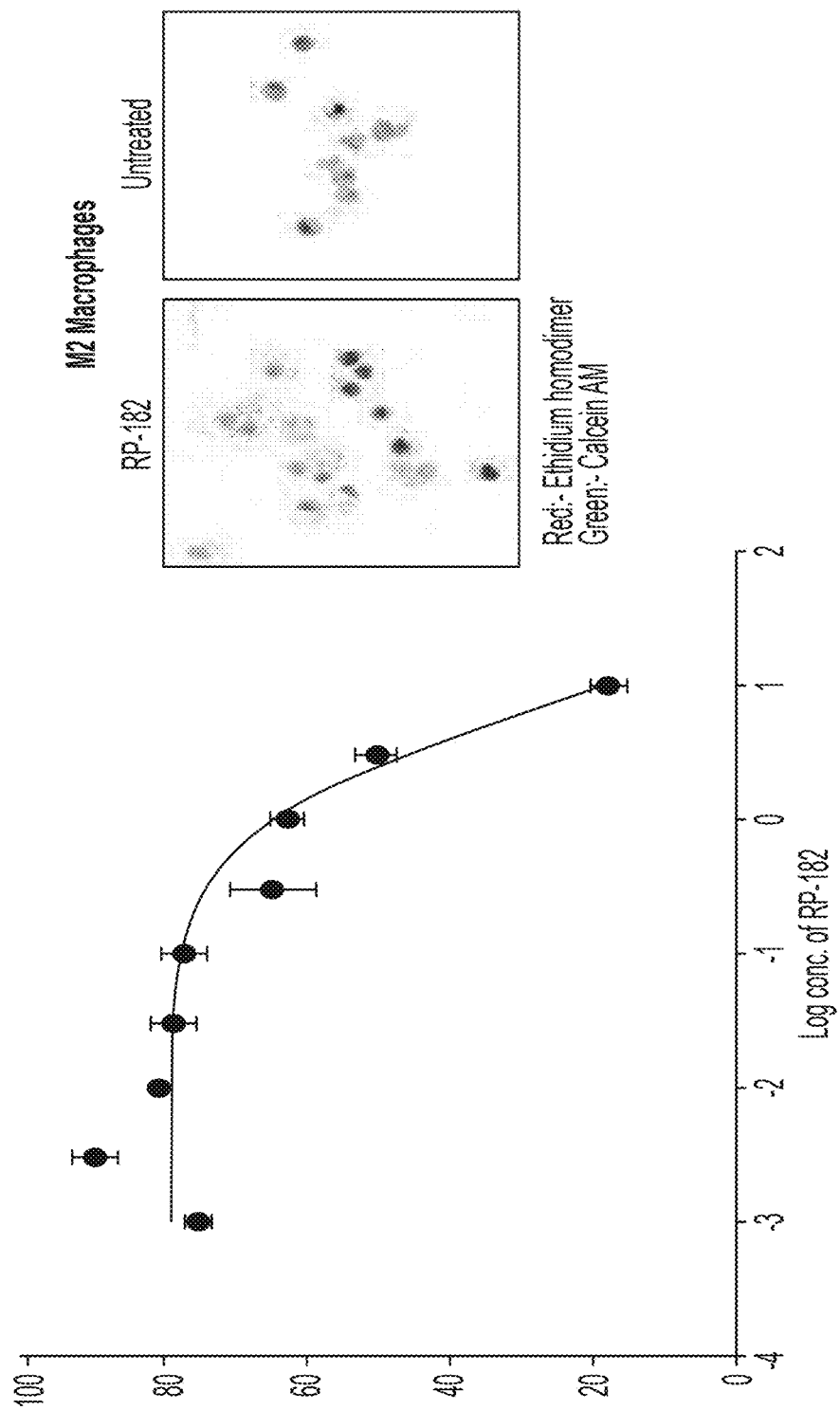
FIG. 20 is a graph for a dose response curve of RP-182 on murine M2 macrophages for cell viability.
Figure 21:
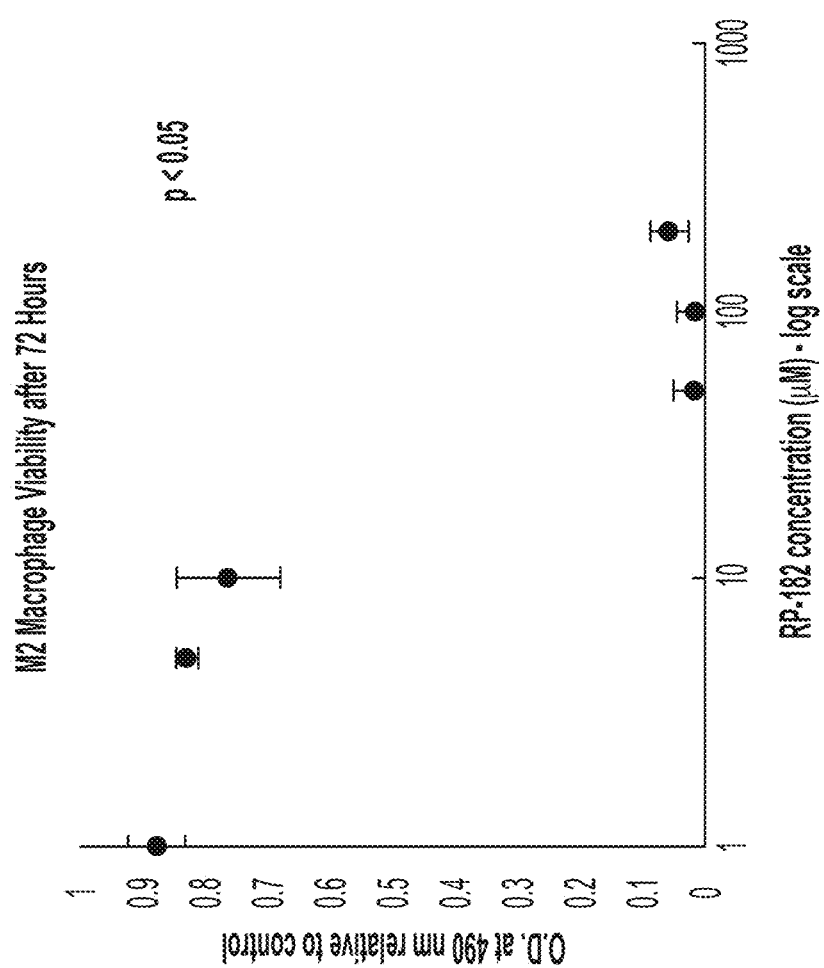
FIG. 21 is a graph showing that RP182 treatment leads to a decrease in M2 macrophage cell viability.

FIG. 16 depicts exemplary results illustrating that RP182 stimulates phagocytosis among M2-like macrophages and TAMs. In FIG. 17, phagocytosis of labeled KPC cells is prominently shown after RP182 treatment, and the results in FIG. 18 show that anti-M2 macrophage activity of RP-182 is CD206 dependent. Notably, apoptotic activity of RP182 treatment remained strong, even when autophagy is blocked, indicating that the activity is a signaling event that is not dependent upon internalization as can be taken from the results in FIG. 19. Finally, FIG. 20 shows a dose response curve of RP-182 on murine M2 macrophages for cell viability, and FIG. 21 demonstrates that RP182 treatment leads to a decrease in M2 macrophage cell viability.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements. Unless the context dictates the contrary, all ranges set forth herein should be interpreted as being inclusive of their endpoints, and open-ended ranges should be interpreted to include commercially practical values. Similarly, all lists of values should be considered as inclusive of intermediate values unless the context indicates the contrary.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise. Moreover, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

Moreover, as used herein, the phrase "at least one of A and B" is intended to refer to 'A' and/or 'B', regardless of the nature of 'A' and 'B'. For example, in some embodiments, 'A' may be single distinct species, while in other embodiments 'A' may represent a single species within a genus that is denoted 'A'. Likewise, in some embodiments, 'B' may be single distinct species, while in other embodiments 'B' may represent a single species within a genus that is denoted 'B'.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method of producing a pharmaceutical agent, comprising:
   identifying a synthetic peptide as a selective binder to carbohydrate recognition domain 4 (CRD4) and carbohydrate recognition domain 5 (CRD5) of CD206;
   quantifying an affinity of the synthetic peptide to the carbohydrate recognition domain 4 (CRD4) and carbohydrate recognition domain 5 (CRD5) of CD206;
   evaluating a variant of a fragment of the synthetic peptide to establish an amino acid substitution;
   preparing a modified synthetic peptide to include the amino acid substitute to thereby produce the pharmaceutical agent, wherein substituting the amino acid increases the affinity to the carbohydrate recognition domain 4 (CRD4) and carbohydrate recognition domain 5 (CRD5) of CD206; and
   contacting a plurality of macrophages with the modified synthetic peptide that includes the amino acid substitute, thereby inducing phagocytic activity and/or inducing of apoptosis in M2 macrophages; and
   wherein the pharmaceutical agent is an RP182 analog selected from the group consisting of SEQ ID NO:2-SEQ ID NO:28.

2. The method of claim 1 further comprising a step of using a molecular model of CD206 in the step of identifying.

3. The method of claim 1 further comprising a step of identifying a conformational change of CD206 upon binding of the pharmaceutical agent.

4. The method of claim 1 further comprising a step of in vitro binding of the pharmaceutical agent to a macrophage.

5. The method of claim 1 wherein the pharmaceutical agent is a RP182 derivative.

6. The method of claim 1 wherein the pharmaceutical agent is an RP182 analog, a bacterial virulence protein or analog thereof, or a collagen variant or analog thereof.

7. A method of shifting a M1/M2 population of macrophages to a population with depleted M2 macrophage content, comprising:
   contacting the M1/M2 population of macrophages with a pharmaceutical agent that targets carbohydrate recognition domain 4 (CRD4) and carbohydrate recognition domain 5 (CRD5) in an amount effective to shift the M1/M2 population of macrophages to the population with depleted M2 macrophage content,
   wherein the pharmaceutical agent is an RP182 analog selected from the group consisting of SEQ ID NO:2-SEQ ID NO:28.

8. A method of activating phagocytosis of tumor associated macrophages, comprising:
   contacting the tumor associated macrophages with a pharmaceutical agent that targets carbohydrate recognition domain 4 (CRD4) and carbohydrate recognition domain 5 (CRD5) in an amount effective to activate phagocytosis of tumor associated macrophages,
   wherein the pharmaceutical agent is an RP182 analog selected from the group consisting of SEQ ID NO:2-SEQ ID NO:28.

9. The method of claim 7 wherein the step of contacting is performed in vivo.

10. The method of claim 8 wherein the step of contacting is performed in vivo.

* * * * *

SEQUENCE LISTING

```
<160> NUMBER OF SEQ ID NOS: 28

<210> SEQ ID NO 1
<211> LENGTH: 10
<212> TYPE: PRT
<213> ORGANISM: Artificial Sequence
<220> FEATURE:
<223> OTHER INFORMATION: Synthetic sequence

<400> SEQUENCE: 1

Lys Phe Arg Lys Ala Phe Lys Arg Phe Phe
1               5                   10

<210> SEQ ID NO 2
<211> LENGTH: 10
```

```
<212> TYPE: PRT
<213> ORGANISM: Artificial Sequence
<220> FEATURE:
<223> OTHER INFORMATION: synthetic sequence

<400> SEQUENCE: 2

Lys Ala Arg Lys Ala Phe Lys Arg Phe Phe
1               5                   10

<210> SEQ ID NO 3
<211> LENGTH: 10
<212> TYPE: PRT
<213> ORGANISM: Artificial Sequence
<220> FEATURE:
<223> OTHER INFORMATION: synthetic sequence

<400> SEQUENCE: 3

Lys Ala Arg Lys Ala Ala Lys Arg Phe Phe
1               5                   10

<210> SEQ ID NO 4
<211> LENGTH: 10
<212> TYPE: PRT
<213> ORGANISM: Artificial Sequence
<220> FEATURE:
<223> OTHER INFORMATION: synthetic sequence

<400> SEQUENCE: 4

Lys Ala Arg Lys Ala Ala Lys Arg Ala Phe
1               5                   10

<210> SEQ ID NO 5
<211> LENGTH: 10
<212> TYPE: PRT
<213> ORGANISM: Artificial Sequence
<220> FEATURE:
<223> OTHER INFORMATION: synthetic sequence

<400> SEQUENCE: 5

Lys Ala Arg Lys Ala Ala Lys Arg Ala Ala
1               5                   10

<210> SEQ ID NO 6
<211> LENGTH: 10
<212> TYPE: PRT
<213> ORGANISM: Ceratitis capitata
<220> FEATURE:
<221> NAME/KEY: MISC_FEATURE
<222> LOCATION: (1)..(10)
<223> OTHER INFORMATION: ceratoxin A

<400> SEQUENCE: 6

Leu Lys Lys Ala Leu Pro Val Ala Lys Lys
1               5                   10

<210> SEQ ID NO 7
<211> LENGTH: 10
<212> TYPE: PRT
<213> ORGANISM: Hyanthria cunea
<220> FEATURE:
<221> NAME/KEY: MISC_FEATURE
<222> LOCATION: (1)..(10)
<223> OTHER INFORMATION: cecropin A

<400> SEQUENCE: 7

Ile Phe Lys Lys Ile Glu Arg Val Gly Gln
1               5                   10
```

```
<210> SEQ ID NO 8
<211> LENGTH: 10
<212> TYPE: PRT
<213> ORGANISM: Hyalophora cecropia
<220> FEATURE:
<221> NAME/KEY: MISC_FEATURE
<222> LOCATION: (1)..(10)
<223> OTHER INFORMATION: cecropin A

<400> SEQUENCE: 8

Leu Phe Lys Lys Ile Glu Lys Val Gly Gln
1               5                   10

<210> SEQ ID NO 9
<211> LENGTH: 10
<212> TYPE: PRT
<213> ORGANISM: Homo sapiens
<220> FEATURE:
<221> NAME/KEY: MISC_FEATURE
<222> LOCATION: (1)..(10)
<223> OTHER INFORMATION: cathelicidin antimicrobial peptide
      preproprotein

<400> SEQUENCE: 9

Phe Phe Arg Lys Ser Lys Glu Lys Ile Gly
1               5                   10

<210> SEQ ID NO 10
<211> LENGTH: 10
<212> TYPE: PRT
<213> ORGANISM: Homo sapiens
<220> FEATURE:
<221> NAME/KEY: MISC_FEATURE
<222> LOCATION: (1)..(10)
<223> OTHER INFORMATION: cathelicidin antimicrobial peptide
      preproprotein

<400> SEQUENCE: 10

Ile Gly Lys Glu Phe Lys Arg Ile Val Gln
1               5                   10

<210> SEQ ID NO 11
<211> LENGTH: 10
<212> TYPE: PRT
<213> ORGANISM: Homo sapiens
<220> FEATURE:
<221> NAME/KEY: MISC_FEATURE
<222> LOCATION: (1)..(10)
<223> OTHER INFORMATION: cathelicidin antimicrobial peptide
      preproprotein

<400> SEQUENCE: 11

Arg Ile Lys Asp Phe Leu Arg Asn Leu Val
1               5                   10

<210> SEQ ID NO 12
<211> LENGTH: 10
<212> TYPE: PRT
<213> ORGANISM: Homo sapiens
<220> FEATURE:
<221> NAME/KEY: MISC_FEATURE
<222> LOCATION: (1)..(10)
<223> OTHER INFORMATION: cathelicidin antimicrobial peptide
      preproprotein

<400> SEQUENCE: 12

Arg Ile Val Gln Arg Ile Lys Asp Phe Leu
1               5                   10
```

```
<210> SEQ ID NO 13
<211> LENGTH: 10
<212> TYPE: PRT
<213> ORGANISM: Xenopus laevis
<220> FEATURE:
<221> NAME/KEY: MISC_FEATURE
<222> LOCATION: (1)..(10)
<223> OTHER INFORMATION: magalinins preproprotein

<400> SEQUENCE: 13

Phe Leu His Ser Ala Lys Lys Phe Gly Lys
1               5                   10

<210> SEQ ID NO 14
<211> LENGTH: 10
<212> TYPE: PRT
<213> ORGANISM: Xenopus laevis
<220> FEATURE:
<221> NAME/KEY: MISC_FEATURE
<222> LOCATION: (1)..(10)
<223> OTHER INFORMATION: magalinins preproprotein

<400> SEQUENCE: 14

His Ser Ala Lys Lys Phe Gly Lys Ala Phe
1               5                   10

<210> SEQ ID NO 15
<211> LENGTH: 11
<212> TYPE: PRT
<213> ORGANISM: pleuronectes americanus
<220> FEATURE:
<221> NAME/KEY: misc
<222> LOCATION: (1)..(11)
<223> OTHER INFORMATION: pleurocidin

<400> SEQUENCE: 15

Phe Phe Lys Ile Cys Ala Ala His Val Gly Lys
1               5                   10

<210> SEQ ID NO 16
<211> LENGTH: 10
<212> TYPE: PRT
<213> ORGANISM: Pseudis paradoxa
<220> FEATURE:
<221> NAME/KEY: MISC_FEATURE
<222> LOCATION: (1)..(10)
<223> OTHER INFORMATION: pseudin-2

<400> SEQUENCE: 16

Ala Leu Lys Lys Val Phe Gln Gly Ile His
1               5                   10

<210> SEQ ID NO 17
<211> LENGTH: 10
<212> TYPE: PRT
<213> ORGANISM: Streptococcus pneumoniae
<220> FEATURE:
<221> NAME/KEY: MISC_FEATURE
<222> LOCATION: (1)..(10)
<223> OTHER INFORMATION: fibronectin binding protein PavA

<400> SEQUENCE: 17

Glu Lys Leu Ser Ala Phe Arg Asn Phe Phe
1               5                   10

<210> SEQ ID NO 18
<211> LENGTH: 10
<212> TYPE: PRT
```

```
<213> ORGANISM: Streptomyces spec.
<220> FEATURE:
<221> NAME/KEY: MISC_FEATURE
<222> LOCATION: (1)..(10)
<223> OTHER INFORMATION: secretion protein

<400> SEQUENCE: 18

Ala Val Arg Arg Leu Ala Gln Arg Leu Ala
1               5                   10

<210> SEQ ID NO 19
<211> LENGTH: 10
<212> TYPE: PRT
<213> ORGANISM: Vibrio vulnificus
<220> FEATURE:
<221> NAME/KEY: MISC_FEATURE
<222> LOCATION: (1)..(10)
<223> OTHER INFORMATION: polar flagellin FlaB

<400> SEQUENCE: 19

Met Val Phe Arg Asp Val Gly Asn Arg Asn
1               5                   10

<210> SEQ ID NO 20
<211> LENGTH: 10
<212> TYPE: PRT
<213> ORGANISM: Chlamydia spec.
<220> FEATURE:
<221> NAME/KEY: MISC_FEATURE
<222> LOCATION: (1)..(10)
<223> OTHER INFORMATION: putative inner membrane protein

<400> SEQUENCE: 20

Lys Glu Phe Leu Ala Phe Lys Arg Phe Phe
1               5                   10

<210> SEQ ID NO 21
<211> LENGTH: 10
<212> TYPE: PRT
<213> ORGANISM: Mycobacterium spec.
<220> FEATURE:
<221> NAME/KEY: MISC_FEATURE
<222> LOCATION: (1)..(10)
<223> OTHER INFORMATION: phage tail tape measure protein

<400> SEQUENCE: 21

Gly Phe Arg Glu Leu Phe Arg Gln Leu Asp
1               5                   10

<210> SEQ ID NO 22
<211> LENGTH: 10
<212> TYPE: PRT
<213> ORGANISM: Acinetobacter baumannii
<220> FEATURE:
<221> NAME/KEY: MISC_FEATURE
<222> LOCATION: (1)..(10)
<223> OTHER INFORMATION: tail protein

<400> SEQUENCE: 22

Ile Glu Asn Ala Ala Phe Lys Arg Phe Phe
1               5                   10

<210> SEQ ID NO 23
<211> LENGTH: 10
<212> TYPE: PRT
<213> ORGANISM: Homo sapiens
<220> FEATURE:
<221> NAME/KEY: MISC_FEATURE
<222> LOCATION: (1)..(10)
```

```
<223> OTHER INFORMATION: pro-alpha collagen

<400> SEQUENCE: 23

Asp Arg Gly Ile Lys Gly His Arg Gly Phe
1               5                   10

<210> SEQ ID NO 24
<211> LENGTH: 10
<212> TYPE: PRT
<213> ORGANISM: Homo sapiens
<220> FEATURE:
<221> NAME/KEY: MISC_FEATURE
<222> LOCATION: (1)..(10)
<223> OTHER INFORMATION: collagen type IV a6 chain

<400> SEQUENCE: 24

Leu Arg Gly Gln Lys Gly Asp Arg Gly Phe
1               5                   10

<210> SEQ ID NO 25
<211> LENGTH: 10
<212> TYPE: PRT
<213> ORGANISM: Homo sapiens
<220> FEATURE:
<221> NAME/KEY: MISC_FEATURE
<222> LOCATION: (1)..(10)
<223> OTHER INFORMATION: collagen type V alpha 3 chain

<400> SEQUENCE: 25

Glu Ala Gly Glu Lys Gly Asp Gln Gly Leu
1               5                   10

<210> SEQ ID NO 26
<211> LENGTH: 10
<212> TYPE: PRT
<213> ORGANISM: Homo sapiens
<220> FEATURE:
<221> NAME/KEY: MISC_FEATURE
<222> LOCATION: (1)..(10)
<223> OTHER INFORMATION: collagen alpha 1 (VII) chain isoform X2

<400> SEQUENCE: 26

His Val Val Gln Arg Gly Glu His Ser Leu
1               5                   10

<210> SEQ ID NO 27
<211> LENGTH: 10
<212> TYPE: PRT
<213> ORGANISM: Homo sapiens
<220> FEATURE:
<221> NAME/KEY: MISC_FEATURE
<222> LOCATION: (1)..(10)
<223> OTHER INFORMATION: collagen alpha 3 (VI) chain isoform X3

<400> SEQUENCE: 27

Val Leu Asp Ala Ile Arg Arg Leu Arg Leu
1               5                   10

<210> SEQ ID NO 28
<211> LENGTH: 10
<212> TYPE: PRT
<213> ORGANISM: Homo sapiens
<220> FEATURE:
<221> NAME/KEY: MISC_FEATURE
<222> LOCATION: (1)..(10)
<223> OTHER INFORMATION: human type XVIII collagen
```

-continued

```
<400> SEQUENCE: 28

Ile Val Arg Arg Ala Asp Arg Ala Ala Val
1               5                   10
```